(12) United States Patent
Quazi

(10) Patent No.: US 11,297,775 B1
(45) Date of Patent: Apr. 12, 2022

(54) LED GROW LIGHT SYSTEM WITH TIME VARYING LIGHT INTENSITY

(71) Applicant: Boulder Lamp, Inc., Lafayette, CO (US)

(72) Inventor: Fazle Quazi, Boulder, CO (US)

(73) Assignee: Boulder Lamp, Inc., Lafayette, CO (US)

( * ) Notice: Subject to any disclaimer, the term of this patent is extended or adjusted under 35 U.S.C. 154(b) by 0 days.

(21) Appl. No.: 17/382,646

(22) Filed: Jul. 22, 2021

(51) Int. Cl.
*A01G 7/04* (2006.01)
*F21S 4/28* (2016.01)
(Continued)

(52) U.S. Cl.
CPC .............. *A01G 7/045* (2013.01); *A61L 2/084* (2013.01); *A61L 2/24* (2013.01); *A61L 2/26* (2013.01);
(Continued)

(58) Field of Classification Search
CPC . A01G 7/045; A01G 9/249; F21S 4/28; F21S 8/06; H05B 47/19; H05B 47/165;
(Continued)

(56) References Cited

U.S. PATENT DOCUMENTS 8,344,659 B2 1/2013 Shimomura et al.
8,680,787 B2 3/2014 Veskovic
(Continued)

FOREIGN PATENT DOCUMENTS

CN 105247957 B 8/2017
CN 105960070 B 9/2017

OTHER PUBLICATIONS

Yonglan Tian et al., "Effects of periodic photoinhibitory light exposure on physiology and productivity of *Arabidopsis* plants grown under low light", Journal of Experimental Botany, Jul. 10, 2017; 68(15): 4249-4262.
(Continued)

*Primary Examiner* — Bao Q Truong
(74) *Attorney, Agent, or Firm* — Patricia C. Brzostowicz; Superioer Patent Group, LLC

(57) ABSTRACT

A LED grow light array and method for controlling thereof, aimed at increasing plant canopy light penetration without stationary hot spots, providing antimicrobial light to eliminate microorganism on plants, providing pulsing canopy penetrating and microbial light without a dark period, and reducing energy consumption, the LED grow light array comprising: a LED grow light array, the array comprising at least four light bars, wherein the light bars comprise discrete photosynthetic LED chips of different types based on the wavelength of light they emit, the light they emit being either blue, red, or white light, or a combination thereof, wherein blue light wavelength ranges from 405 nm to 450 nm, red light wavelength ranges from 630 nm to 720 nm, and white light is a combination of wavelengths that ranges from 400 nm to 700 nm, each type of photosynthetic LED chip forming a set of chips; wherein the bars are in a series and spaced evenly over a given plant growing area; wherein the light bars further comprise discrete antimicrobial LED chips of different types based on the wavelength of light they emit, the light being light with antimicrobial properties between the wavelengths of 100 nm and 405 nm, each type forming a set of chips; wherein each light bar comprises a circuit board to mount said discrete photosynthetic and antimicrobial LED chips thereon; at least one LED driver to provide power to the LED chips; at least one microprocessor to control the at least one LED driver; and a lighting program sent to the microprocessor designed to control the at least four light bars and the sets of photosynthetic and antimicrobial LED chips individually.

31 Claims, 28 Drawing Sheets

(51) Int. Cl.
| | |
|---|---|
| *H05B 47/19* | (2020.01) |
| *F21V 23/00* | (2015.01) |
| *H05B 47/165* | (2020.01) |
| *A61L 2/08* | (2006.01) |
| *A61L 2/24* | (2006.01) |
| *A61L 2/26* | (2006.01) |
| *F21Y 115/10* | (2016.01) |
| *F21Y 113/10* | (2016.01) |
| *F21S 8/06* | (2006.01) |
| *A01G 9/24* | (2006.01) |

(52) U.S. Cl.
CPC .............. *F21S 4/28* (2016.01); *F21V 23/005* (2013.01); *H05B 47/165* (2020.01); *H05B 47/19* (2020.01); *A01G 9/249* (2019.05); *A61L 2202/11* (2013.01); *A61L 2202/14* (2013.01); *F21S 8/06* (2013.01); *F21Y 2113/10* (2016.08); *F21Y 2115/10* (2016.08)

(58) Field of Classification Search
CPC ... A61L 2/084; A61L 2/24; A61L 2/26; A61L 2202/11; A61L 2202/14; F21V 23/005; F21Y 2113/10; F21Y 2115/10
See application file for complete search history.

(56) References Cited

U.S. PATENT DOCUMENTS

| | | | |
|---|---|---|---|
| 8,742,695 | B2 | 6/2014 | Wray |
| 9,028,096 | B2 | 5/2015 | Verdes et al. |
| 9,210,753 | B2 | 12/2015 | Williams et al. |
| 9,288,861 | B2 | 3/2016 | Williams et al. |
| 9,442,478 | B2 | 9/2016 | Barrenscheen et al. |
| 9,681,504 | B1 | 6/2017 | Barbosa |
| 9,763,298 | B2 | 9/2017 | Weeks et al. |
| 10,918,747 | B2 | 2/2021 | Barron et al. |
| 2002/0021568 | A1 | 2/2002 | Wardenburg |
| 2013/0271993 | A1 | 10/2013 | Jan |
| 2015/0116997 | A1 | 4/2015 | Tappert et al. |
| 2016/0192598 | A1 | 7/2016 | Haggarty |
| 2018/0359834 | A1* | 12/2018 | Duong .................. H05B 45/52 |
| 2019/0098842 | A1* | 4/2019 | Barber, III ............. A01G 7/045 |
| 2019/0335675 | A1* | 11/2019 | Ngo ...................... F21V 23/007 |

OTHER PUBLICATIONS

Akvil E Viršil et al., "The Comparison of Constant and Dynamic Red and Blue Light Irradiation Effects on Red and Green Leaf Lettuce", Published: Nov. 17, 2020, Agronomy, EISSN 2073-4395, Published by MDP.

Jonathan Gillespie et al., "Efficacy of pulsed 405-nm Light-Emitting Diodes for Antimicrobial Photodynamic Inactivation: Effects of intensity, Frequency, and Duty Cycle" Photomedicine and Laser Surgery, vol. 35, No. 3, 2017.

M. Kanechi et al., "Effects of pulsed lighting based light-emitting diodes on the growth and photosynthesis of lettuce leaves", International Society for Horticultural Science, ISHS Acta Horticulture 1134: VIII International Symposium on Light in Horticulture.

Michio Kanechi, "Growth and Photosynthesis under Pulsed Lighting", Sep. 19, 2018, DOI: 10.5772/intechopen.75519.

Michelle Maclean et al., "A New Proof of Concept in Bacterial Reduction: Antimicrobial Action of Violet-Blue Light (405 nm) in Ex Vivo Stored Plasma", Hindawi Publishing Corporation, Journal of Blood Transfusion, vol. 2016, Article ID 2920514.

Chukuka S Enwemeka, "Antimicrobial Blue Light: An Emerging Alternative to Antibiotics", Photomedicine and Laser Surgery, Oct. 2013.

Jeff Gavin, "Sanitizing Light: LEDs Becoming a Disinfectant Technology", Electrical Contractor, Published on May 15, 2019.

Valeria Angarano et al., "Visible Light as an Antimicrobial Strategy for Inactivation of *Pseudomonas fluorescens* and *Staphylococcus epidermidis* Biofilms", Antimicrob Resist Infect Control 8, 14 (2019). https://doi.org/10.1186/s13756-019-0470-1.

Jeswal, Punam, "Mechanisms of Photosynthesis" Plant Physiology, B.Sc (Hons.) Part III.

Lysenko et al. "Far-Red Spectrum of Second Emerson Effect: A Study Using Dual-Wavelength Pulse Amplitude Modulation Fluorometry" American Journal of Biochemistry and Biotechnology, Nov. 19, 2014.

* cited by examiner

LED GROW LIGHT SYSTEM WITH TIME VARYING LIGHT INTENSITY

The following application is an application for patent under 35 USC 111 (a).

FIELD

This disclosure relates to the field of indoor plant growth and technologies to increase photosynthesis, reduce mold growth and energy consumption via an improved light-emitting diode (LED) control method.

BACKGROUND

An indoor LED, a light emitting-diode, being a semiconductor diode which glows when a voltage is applied, grow light for supporting plant growth generally consists of a series connected LEDs emitted various wavelengths of light. These LEDs or LED chips are soldered to a printed circuit board (PCB) and connected to one or multiple LED drivers which supply power. The LED drivers are controlled by microprocessors.

An LED array may include multiple light bars each comprising identical PCBs, generally at least one inch to a foot wide and two, three, four, or even six or eight feet (ft) long, with soldered LED chips, mounted on heat sinks with appropriate drivers and processors. These may be hung above growing plants in rows. A single PCB-based high power indoor grow light for large growing areas may be made of hundreds of discrete LEDs fixed to PCBs of at least a half foot wide by 1 foot long, or 1 ft by 1 ft, 2 ft×2 ft, or as large as 8 ft×8 ft. These are termed quantum board/dots LED grow lights, wherein a large number of small LED chips, being hundreds to thousands, are fixed to a PCB along with the heat sink, driver, and microprocessor to keep cost of the lighting structure low.

Although a quantum board/dots LED grow light costs less, it has many disadvantages. It creates hot spots, intense light in a small area, especially near the center of the light fixture. Hot spots can burn plant leaves causing damage to the plant and therefore reduce plant production. Light patterns generated by a quantum board/dots LED grow lights also lack uniformity. They produce more light in the center of the grow area below fixture and much less near the edges of the growing area.

LED arrays with multiple light bars are more expensive but less likely to create hot spots. Light spread may be more uniform but light intensity tends to decrease at the edges of the growing area. Decreased light intensity reduces photosynthesis, and therefore reduces plant growth and crop yield. LED grow lights in general have additional problems such as poor light penetration deep into plant canopy. Light penetration requires more intense light which incurs more energy consumption burdening production by increasing costs, and society by increasing energy usage. Additional challenges in the greenhouse or indoor grow industry are mold, fungi, and bacterial control. UV light can be used to reduce microorganism, however, a long exposure to stationary UV light may be harmful to humans tending the plants.

What is needed in the art is an LED grow light with a combination of photosynthetic and antimicrobial light which distributes light evenly, penetrates the plant canopy, and eliminates hot spots to promote photosynthesis, and therefore crop yield, without increasing energy consumption, and in addition reduces unwanted microbial growth that harms plants without harming humans tending the plants.

SUMMARY

This present disclosure is an LED grow light array, and method for controlling an LED grow light array, with a combination of photosynthetic promoting and antimicrobial light which distributes light evenly, penetrates the plant canopy, and eliminates hot spots to promote photosynthesis, and therefore crop yield, without increasing energy consumption, and in addition reduces unwanted microbial growth that harms plants without harming humans tending the plants.

As such, the LED grow light array for increasing plant canopy light penetration without increasing energy consumption, providing antimicrobial light to eliminate microorganism on plant, providing pulsing canopy penetrating and microbial light without a dark period, the LED grow light array comprises: a LED grow light array, the array comprising at least four light bars, wherein the light bars comprise discrete photosynthetic LED chips of different types based on the wavelength of light they emit, the light they emit being either blue, red, or white light, or a combination thereof, wherein blue light wavelength ranges from 405 nm to 450 nm, red light wavelength ranges from 600 nm to 720 nm, and white light is a combination of wavelengths that ranges from 400 nm to 700 nm, each type of photosynthetic LED chip forming a set of chips; wherein the bars are spaced evenly over a given plant growing area; wherein the light bars further comprise discrete antimicrobial LED chips of different types based on the wavelength of light they emit, the light being light with antimicrobial properties between the wavelengths of 100 nm and 405 nm, each type forming a set of chips; wherein each light bar comprises a circuit board to mount said discrete photosynthetic and antimicrobial LED chips thereon; at least one LED driver to provide power to the LED chips; at least one microprocessor to control the at least one LED driver; and a lighting program sent to the microprocessor designed to control the at least four light bars and the sets of photosynthetic and antimicrobial LED chips individually. The microprocessor may be configured for wireless communication and lighting program delivered wirelessly.

Further, the antimicrobial LED chips of the array may not be powered unless specified by the lighting program. The lighting program may designate different amounts of energy to be provided to the outer and inner light bars of the array. The lighting program may designate that the outer light bars receive more continuous power than the inner light bars. The lighting program may designate that the light bars, in sequential order, receive increased amounts of power for a given amount of time. The lighting program may repeat the sequential order of designating increase amounts of power for a given amount of time. The lighting program may repeat, in reverse order, the sequential order of designating increase amounts of power for a given amount of time. The given amount of time may be at least 0.000005 seconds.

Further, a lighting program may designate that the light bars receive at least two pulses of additional power for either the photosynthetic LED chips or antimicrobial LED chips in a row beginning with the first light bar and moving to the next light bar sequentially, the pulses being at least 0.000005 seconds each. The lighting program may designate that the light bars receive at least three pulses of additional power in a row beginning with the first light bar and moving to the next light bar sequentially, the pulses being at least 0.000005 seconds each. The lighting program may designate that the light bars receive at least four pulses of additional power in a row beginning with the first light bar and moving to the next light bar sequentially, the pulses being at least 0.000005 seconds each.

Moreover, a lighting program may designate an initial power feed to all the light bars and therein after designates increased power to each light bar in sequential order for a given period of time. The lighting program may designate an initial power feed to all the light bars and therein after designates increased power to the interior light bars in sequential order for a given period of time. The lighting program may designate a higher initial power feed to the outside light bars than the inside light bars.

Inasmuch, a lighting program may designate a higher power feed for the set of photosynthetic LED chips emitting 660 nm for a given period of time in each bar sequentially. The given period of time may be at least 0.05 seconds. The lighting program may designate a higher power feed for the set of photosynthetic LED chips emitting 730 nm for a given period of time in each bar sequentially. The given period of time may be at least 0.05 seconds. LED chips emitting wavelengths of 450 nm or 385 nm may be powered differentially for a give period of time in each bar sequentially, being designated higher power feed than other LED chips for various periods of time.

Further, a lighting program may designate that at least some photosynthetic LED chips are powered and at least one set of antimicrobial LED chips are powered on for each light bar sequentially with at least 1 watt for at least 0.000005 seconds.

Further, a lighting program may designate that an initial power amount for the photosynthetic LED chips in all light bars for a $1^{st}$ set time period, thereafter power to the photosynthetic LED chips in at least one light bar is increased to a level 2 power amount for a $2^{nd}$ set time period, thereafter power to the photosynthetic LED chips in the at least one light bar is increased to a level 3 power amount for a $3^{rd}$ set time period, and thereafter the power to the photosynthetic LED chips in the at least one light bar is reset to the initial power amount. These time periods may be as little as 0.05 seconds for photosynthetic LED chips, or 0.5 s, or 1 s, or 2 s, or 3 s, or 4 s, or 5 s, or 10 s, or 20 s, or 30 s, or more. Power increases for photosynthetic LED chips may be at least 1 W, or 5 W, or 10 W, or 20 W, or 40 W, or 50 W, or 100 W, or 150 W, or 200 W, or 250 W, or more.

The same lighting program may additionally designate that a pulse of power is sent to the antimicrobial LED chips in each light bar in sequence for a time period of at least 0.000005 s, or at least 0.00005 s, or at least 0.0005 s, or 0.005 s, or 0.05 s, or 0.5 s, or 1 s, or more. Or the same lighting program may designate that after the power to the photosynthetic LEDs in the at least one light bar is increased to the level 2 power for the $2^{nd}$ set time period, power to the photosynthetic LEDs of a next light bar in the sequence is increased to the level 2 power for the $2^{nd}$ set time period, and thereafter power to the photosynthetic LED chips in the next light bar is increased to the level 3 power amount for the $3^{rd}$ set time period, and thereafter the power to the photosynthetic LED chips in the next light bar is reset to the initial power amount. Power increases for antimicrobial LED chips may be at least 1 W, or 2 W, or 5 W, or 10 W, or 20 W, or 40 W, or 50 W, or more. Power increases to sets of photosynthetic LEDs and antimicrobial LEDs may be continuous in nature.

Even further, a method for lighting a grow area is presented. The method comprises: providing a LED grow light array, the array comprising at least four light bars spaced evenly over the grow area, wherein the light bars comprise discrete photosynthetic LED chips of different types based on the wavelength of light they emit, the light they emit being either blue, red, or white light, or a combination thereof, wherein blue light wavelength ranges from 405 nm to 450 nm, red light wavelength ranges from 600 nm to 720 nm, and white light is a combination of wavelengths that ranges from 400 nm to 700 nm, each type of photosynthetic LED chip forming a set of chips; providing on the light bars discrete antimicrobial LED chips of different types based on the wavelength of light they emit, the light being light with antimicrobial properties between the wavelengths of 100 nm and 405 nm, each type forming a set of chips, wherein the antimicrobial LED chips are not powered unless specified by the program; providing a driver to power the light bars and discrete sets of LED chips; providing a microprocessor to control the driver, the microprocessor capable of receiving a lighting program which designates how the driver is controlled; and providing a lighting program designed to control the at least four light bars and the sets of photosynthetic and antimicrobial LED chips individually.

Figure 1A:
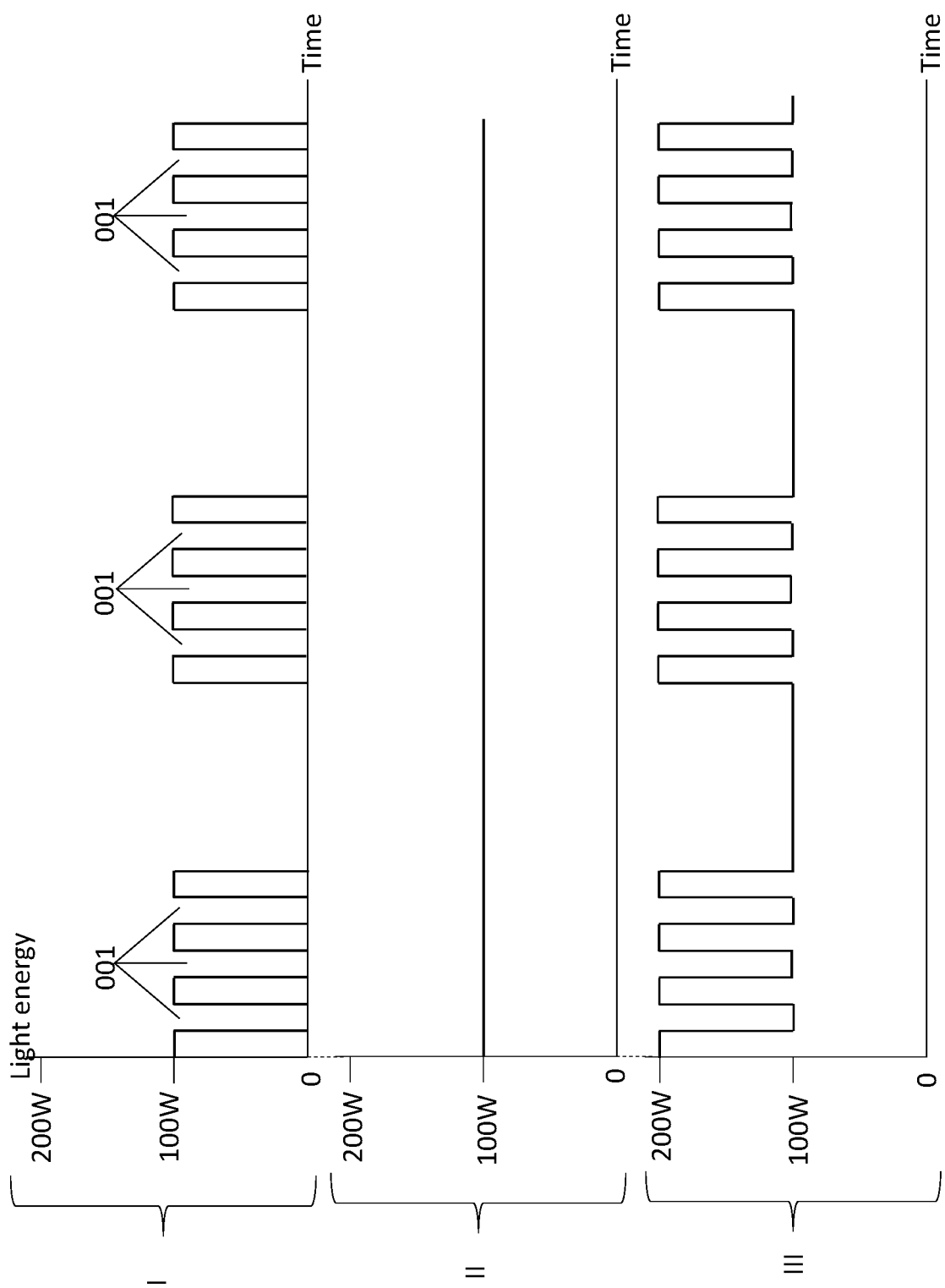
FIG. 1A illustrates differences between prior art pulsing and pulsing of the present disclosure.

Before explaining the disclosed embodiments of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION

In the disclosed LED array and method of growing plants using an LED array, being a grow environment where multiple grow lights are used, the light levels of all or some of the LED bars in these grow lights are in some instances preadjusted to operate at a lower intensity than their respective maximum light delivery capacity. Light intensity or level is adjusted or attenuated by amount of energy or power in watts (W) provided to the LEDs in a bar. Thereafter, periodically and in sequence, light levels of each or selected number of grow light bars are increased.

In the current state of the art, a typical commercial grow table is 4 feet wide and 8 feet long. The number of grow tables used in a single building of a commercial grow facility depends on the size of the grow space. If a 4-bar LED array that has a footprint of 4 ft by 4 ft is used then it will require two 4-bar lights over a 4 feet by 8 feet grow table. In this case the total number of LED grow bars is 8. LEDs in a 4-bar LED array grow light that provide an average 800 PPFD typically consume 600 W of energy, each bar consumes 150 W. Since a 4 feet by 8 feet grow table has 2 lights, the total typical LED energy consumption will be 1,200 W.

In the present disclosure, in order to improve light output from an LED array, the individual light bars may be designed with a lighting program to deliver an increased or decreased amount of power than the traditional 150 W, for instance 200 W, or 100 W, to one or more of the LED light bars at different times within the lighting program as described herein. In one arrangement bars 1 and 8, or exterior bars, can be set to 200 W each. This will increase light intensity at both ends of the grow table. For the six interior, or inside LED bars, bars 2-7, the nominal energy sent to each may be 100 W. Reduced energy feed reduces light in the middle of the grow table, thus eliminating stationary hot spots. After an initial period of time, the controllers may be programmed to cycle additional power to bars 2-7, in one example, for about 20 seconds. This increase and/or decrease in delivered wattage to the bars can be periodic in nature, and may be programmed to step-increase light intensity, adding for instance 50 W, 100 W, 150 W, 200 W or more, for a set time period, starting at one end of the grow table and moving to the other end. Thereafter, a new cycle will begin. For instance inside LED bars is running with 100 W continuous and 150 W step energy, totaling 250 W energy, at that instant, the light intensity in the surrounding area under the bar will increase causing more canopy light penetration. This will increase photosynthesis. As opposed to the normal 1200 W consumption of a 4 LED bar grow light, the overall energy consumption of 4 LED bar grow light at any given time will be 1,150 W.

The energy consumption can be further reduced if the periodic increase of energy is provided in the form of pulsed energy increase. Pulsed type of energy will have many on and off cycles. Since, each LED bar will have certain amount of continuous power at all times for maintaining continuous photosynthetic activity, there will be no dark period during off cycle of pulsed energy as is with prior art pulsing arrangement. This is illustrated in FIG. 1A. Graph I shows the prior art pulsing method which includes dark periods 001 where no light is delivered. Graph II shows the example wherein 100 W is provided over the entire cycle. Graph III shows an example of 100 W continuous power with additional 100 W pulses that eliminates dark periods. The magnitude of step energy increase and its sequence, duration, pulsing, etc., are controlled by means of a programmable dimming controller that sends instructions to the LED driver that supplies power to the LED bars and/or individual LED chips. For wireless communications, a receiver can be integrated in the controller. Wireless communication permits mobile and laptop lighting control applications.

Various embodiments of the disclosure provided herein include LED grow lights and LED grow light arrays where light levels of all or some of these LED grow light bars are preadjusted to operate at a light intensity which is lower or higher than the prior art or "normal" delivery capacity by changing energy wattage to individual light bars or LED chips. Depending on the desired lighting scheme, the preadjusted light intensity can be lower or higher than nominal light intensity of said grow lights of the prior art. Preset light levels of one or more grow light bars are increased periodically by means of the programmable light/dimming controller. For wireless communications, a receiver can be integrated in the light/dimming controller. Wireless communication permits programming via mobile applications, laptop computing devices or CPUs connected wireless or in a wired fashion to the internet and/or to a WI-FI system.

LEDs are durable, high-power devices capable of providing energy-efficient illumination and varying wavelengths of light from ultra-violet, to visible, to far red. All LED lights share the same basic structure. They consist of a semiconductor chip, or LED chip which produces the light when current flows through it. LED chips produce different color light by using various materials as proton donors, a P-type material, and electron sinks, an N-type material. Applying electric current to the diode pushes the atoms in both materials towards the junction area. When the two materials meet at the junction area, the release of protons in the atoms of the P-type material produces photons of light. Using different P-type materials produces light of different colors. For instance, red and amber LEDs use the aluminum indium gallium phosphide (AlInGaP) materials system. Blue, green and cyan LEDs use the indium gallium nitride (InGaN) system. Together the AlINGaP and INGaN core almost the entire light spectrum, with a gap at green-yellow and yellow. One method of achieving a larger spectrum of colors is to mix different color LEDs in the same device. Combining red, green, and blue LEDs in a single LED device, such as a lighting fixture or mutli-chip LED, and controlling their relative intensities can produce millions of colors. Additionally, combining red, green, and blue in equal amounts produces white light. To be used for efficient illumination of large areas, LEDs are integrated into arrays that incorporate optics, LED drivers, power supplies, and thermal management (heat sinks).

Wavelengths of light effective for promoting photosynthesis may include red light from 600 nanometers (nm) to 700 nm, and above including far red of 700 nm to 850 nm, especially 730 nm, and blue light from 380 nm to 500 nm. Broad spectrum lighting includes the 380 nm to 740 nm range. Different wavelengths and intensity of light may be good for different stages of plant life including the vegetative stage, where blue lights are beneficial, where the plant itself is growing in size, and blooming/flowering, where red light is especially beneficial. Small vegetative plants may require less light with a minimum of 10 photosynthetic photon flux density (PPFD) or $\mu mol/m^2/s$ of photons, or 20 PPFD, or 30 PPFD, or 40 PPFD, or 50 PPFD the first week of growth. For each week of growth this may double, with a vegetative phase in general lasting one to four weeks depending on type of plant, During the flowering and fruit production phase light requirements continue to be in the range of 300 to 400 PPFD or more. Photosynthetic photon flux density (PPFD) is the amount of photosynthetically active photons (400 nm-700 nm) hitting a surface per unit area per unit time.

Wavelengths of light that have been found to be deterrent to harmful bacteria, molds, and fungi that may infect plants include ultra-violet (UV) light with wavelengths of about 425 or less. UV light ranges from 100 nm to about 400 nm with UV-A from 400 to 315 nm, UV-B from 315 to 280 nm, UV-C from 280 to 200 nm, and Vacuum UV from 200 to 100 nm. UV light can be harmful to human skin, especially UV-B and UV-C, and is therefore used with caution. At this time UV-A LED lights are relatively inexpensive and readily available while UV-B and UV-C LEDs are cost prohibitive. However with advances in technology UV-B and UV-C LEDs may become more readily available and cost effective for the indoor plant growing industry.

Two type of operations may use LED grow lights. Greenhouses may use natural light for entire growth period and supplement with artificial lights such as LED grow lights during winter when days are shorter. Indoor grow houses would be self-contained and dependent completely on artificial lights for plant growth. Therefore, it is necessary that these plants receive the best range of light to support photosynthesis and limit harmful bacteria, mold, and/or fungus growth. In order to do this in the most cost-effective and environmentally conscious way it is desired that energy consumption be held to a minimum. The LED grow light array and method of lighting plants of the present disclosure achieve these three goals simultaneously, a goal not achieved by prior art designs.

Figure 1B:
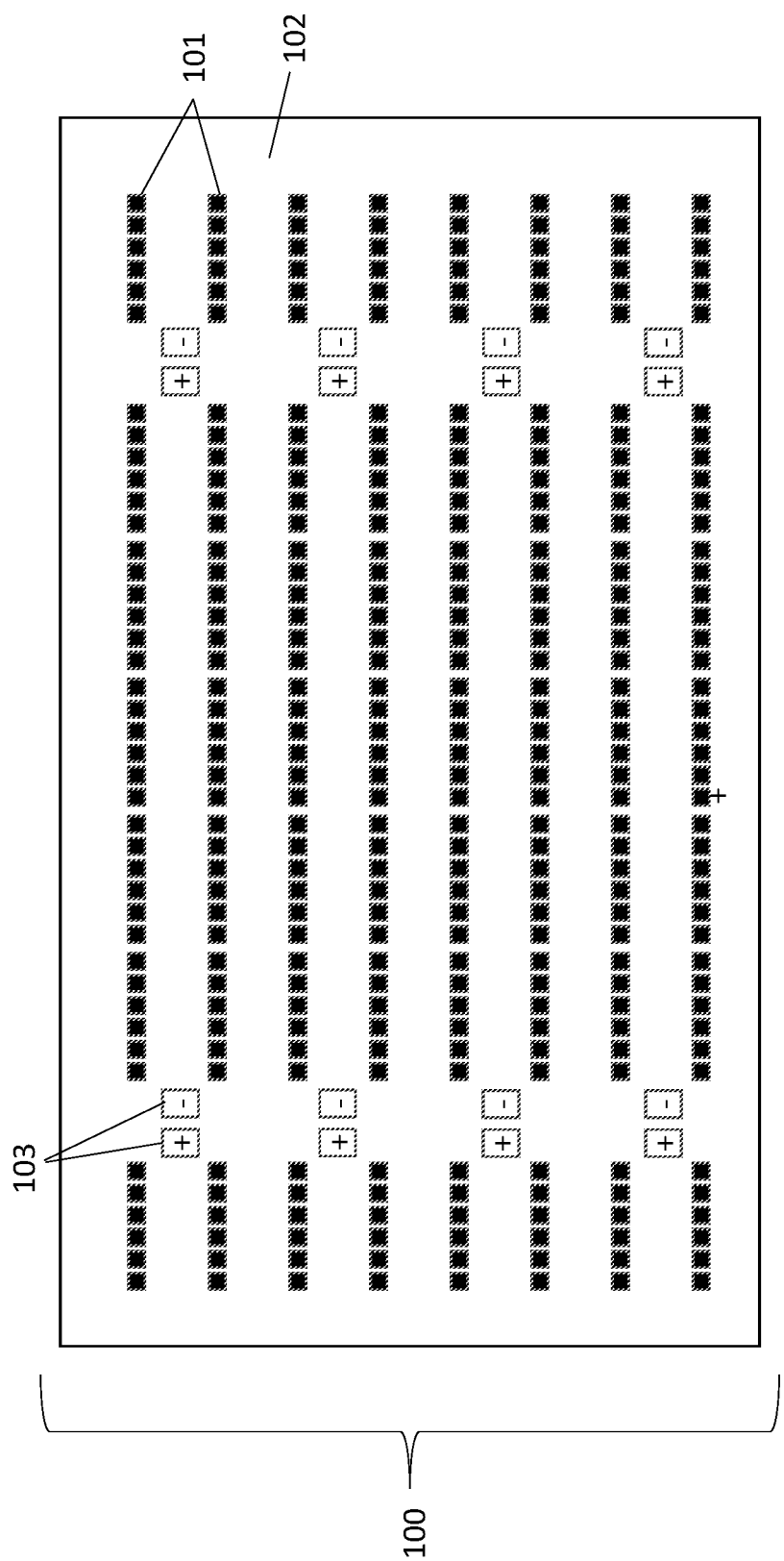
FIG. 1B is an illustration of a prior art quantum type LED grow light PCB board.

To illustrate the difference between prior art designs and the present disclosure, a prior quantum dots (QD) LED grow light is illustrated in FIG. 1B. The QD LED grow light 100 utilizes a collection of individual LEDs 101 soldered on the single PCB 102 to keep cost low. DC current is supplied to the board through connectors 103. The LEDs themselves are small, being 1-2 millimeter (mm) by 1-2 mm in size. These PCBs are generally 2 feet (ft) by 3 ft in size, but may be 3×4 ft, or other sizes. The PCB 102 is mounted on a metal heat sink (not shown) to form a grow light that can hang above plants. These grow lights are designed to illuminate about a 4 ft by 4 ft grow area, depending on number of LEDs.

Although a QD LED grow light costs less, it has many disadvantages. It creates hot spots, small areas of intense light, especially near the center of the light fixture, due to the additive property of light. These hot spots can burn plant leaves. In addition, light patterns generated by a quantum grow lights lacks uniformity, producing more light in the center of the grow area where the fixture may be located, and much less near the edges of the growing area.

Figure 2:
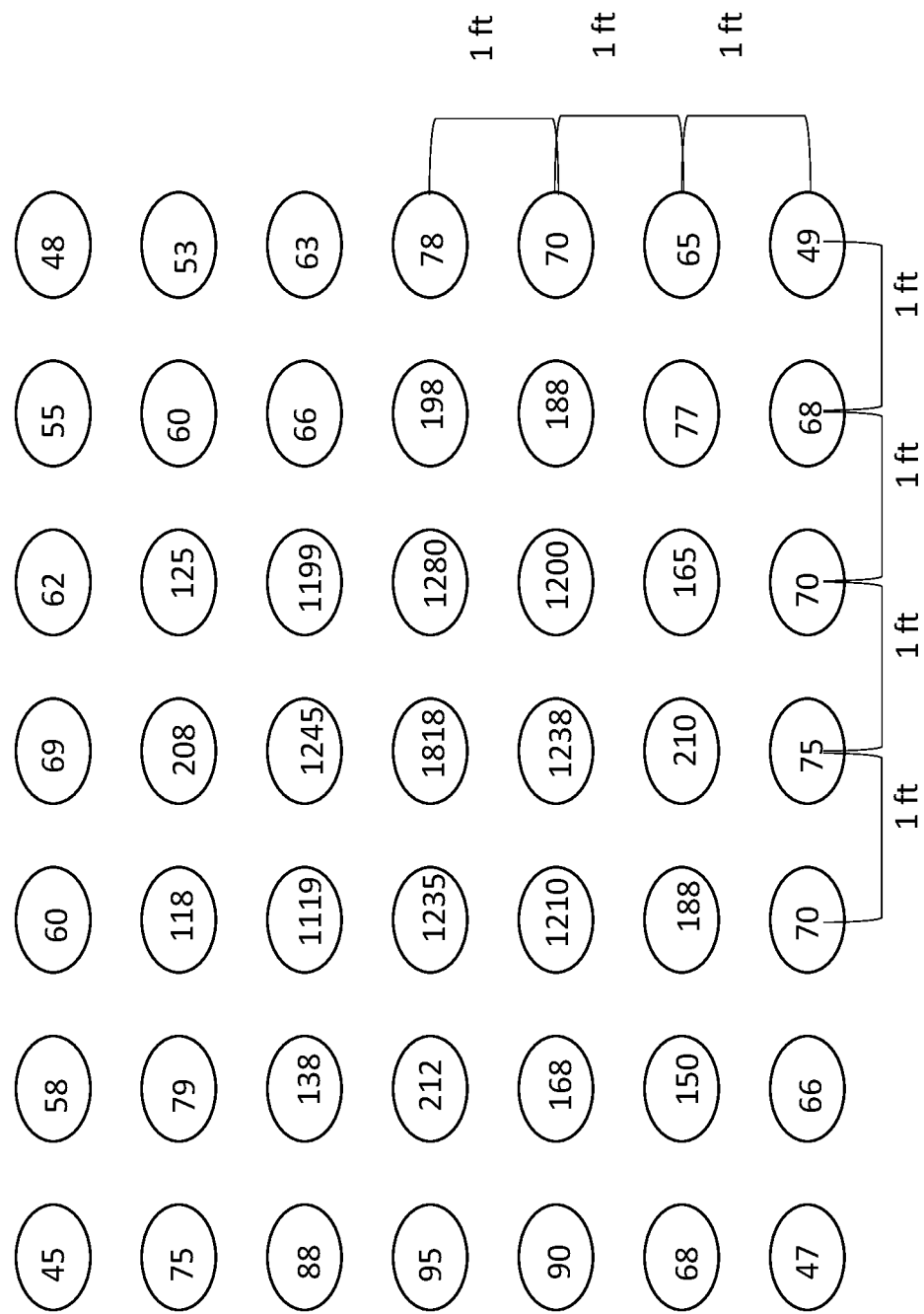
FIG. 2 depicts photosynthetic photon flux density (PPFD) data generated by a prior art quantum type LED grow light.

FIG. 2 is an example of photosynthetic photon flux density (PPM) data generated by a prior art QD LED grow light, similar to that of FIG. 1B. The PPFD was measured over a 3 feet out from the center of the growing area in the x and y axis directions and at a distance of 1 ft below the light. The QD LED used in this test contained 496 LEDs FIG. 1B, 101. Wattage supplied to the QD LED was 400 W. As defined above, photosynthetic photon flux density (PPFD) is the amount of photosynthetically active photons (400-700 nm) hitting a surface per unit area per unit time. PPFD is reported in units of µmol per $m^2$ per second (s) or µmol/$m^2$/s of photons. Optimal growing conditions vary by plant but generally range from 50 PPFD when the plant is small and in the vegetative growth phase, to 500 PPFD, during the flowering and fruit producing state up to 1200 PPFD for some applications. As can be seen in FIG. 2, the PPFD data generated by the QE LED indicates that the center, 2 ft by 2 ft, area received between 1100 and over 1800 PPFD. One foot from this area the PPFD dropped to between about 60 and about 200 PPFD. Three feet from the center the PPFD dropped to between about 50 to 100 PPFD, with corners of the growing area receiving lowest PPFD. In short, plants in the middle of the growing area would receive hot spots of too much light and plants on the edges wouldn't receive enough.

Figure 3:
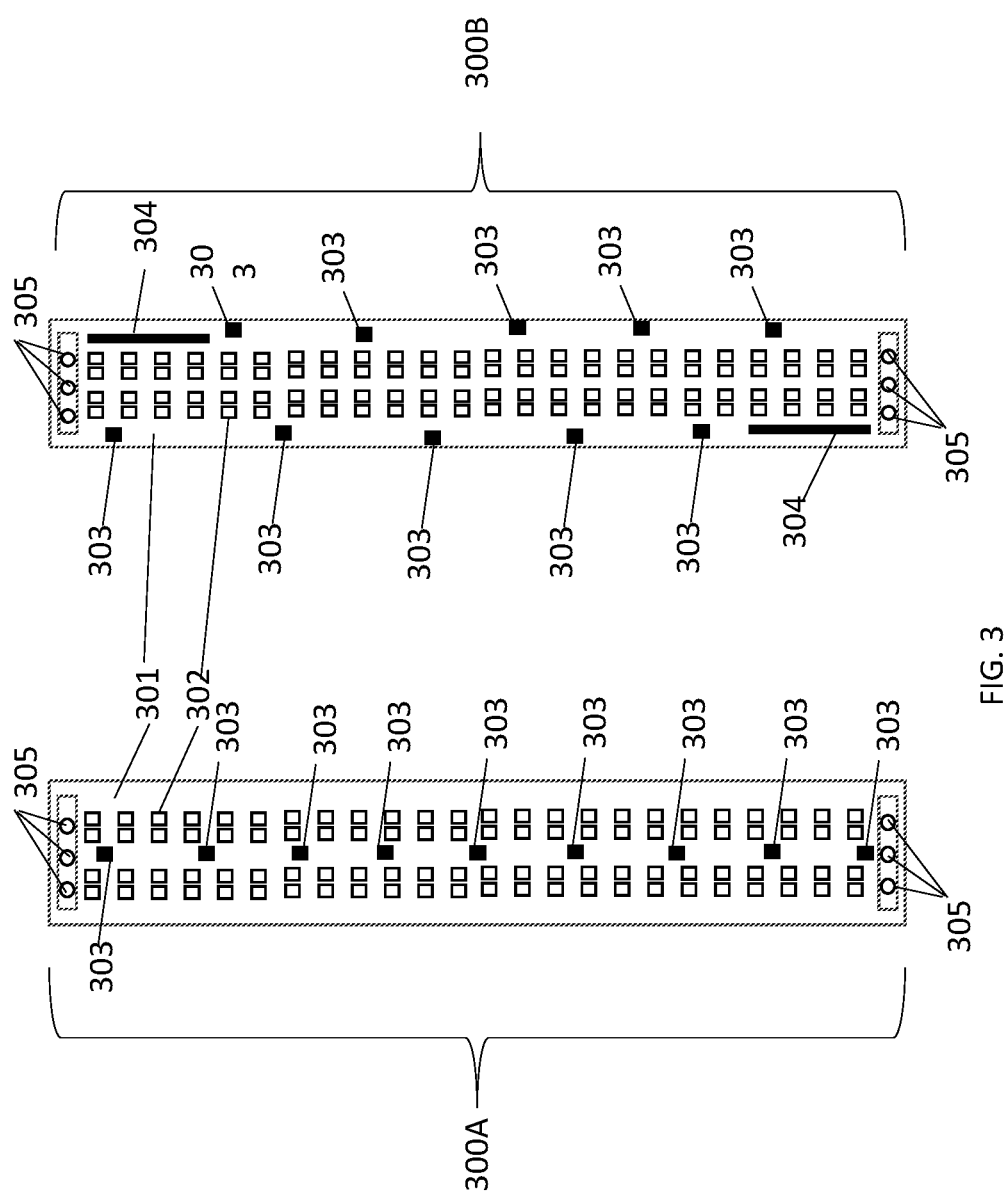
FIG. 3 is one embodiment of a LED light array bar of the present disclosure.

In contrast to the QD grow light of FIG. 1B, the present disclosure describes an array of light bars having smaller number of LEDs on each light bar with light bars spaced evenly over a growing area capable of varying energy consumption of each light bar independently, and/or varying energy consumption of individual LED chips, and therefore eliminating hot spots and improving light uniformity and penetration of light deep into the plant canopy, while saving energy. In addition, the light bars incorporate UV and blue LED chips for providing sweeping antimicrobial light. FIG. 3 illustrates a first 300A and second 300B embodiment of a single printed circuit board (PCB) LED chip array 300A,B of the present disclosure. A PCB 301 is fitted with many individual LED chips 302 via soldering. These LED chips 302 produce light when supplied with DC current. The LED chips 302 may produce various colors of photosynthetic light, or light wavelengths that promote photosynthesis, being photosynthetic LED chips 302, depending on application or grow cycle. Photosynthetic light may include but not be limited to various red lights including far red of 730 nm, blue light, and white light. Additionally, antimicrobial LED chips 303 may provide light in the blue to UV range of 405 nm or less. As shown in FIG. 3, the ratio of photosynthetic LED chips 302 to antimicrobial LED chips 303 may be 10 to 1. This ratio may vary with application and need and may span from 100 to 1, to 50 to 1, to 20:1, to 5:1.

In the PCB LED chip arrays 300A,B of FIG. 3, LED chip to chip interconnecting wires, being embedded circuitry made of PCB traces (not shown), which may be copper, connect LED chips 302,303 to PCB mounted connectors 305 for making connection with external LED drivers 304 that convert AC power to DC power to supply to the LEDs 302, 303. Drivers 304 may be mounted for instance on the heat sink, a housing (not shown), or elsewhere. White and red LED chips 302 may be powered by separate LED drivers. This is because forward voltage drop of white LED chips are significantly different than the forward voltage drop of red LEDs. Other hardware and attachment means, such as to attach the PCB 301 to a heat sink, may be included.

Inasmuch as the PCB LED chip arrays 300A,B of FIG. 3 are shown with four long columns of 4 LED chips 302, 303 in each row, alternate patterns of LED chips 302, 303 such as one column, or two columns, or five columns or more may be appropriate and is encompassed by the present disclosure. Also the design is not limited to the number of rows, being a horizontal or vertical arrangement. Other patterns for LED chip 302,303 placement including but not limited to circular, rectangular, square, or the absence of a pattern, may be formed by the soldered LED chips 302, 303. Additionally arrays may be formed from chip on board (COB) LEDs. COB LEDs are multiple LED chips, typically nine or more, bonded onto a substrate to form a single module.

A full spectrum LED PCB array, having light in the 400 nm to 700 nm wavelengths, may be manufactured with various LED chips, being photosynthetic LED chips 302, FIG. 3, as well as antimicrobial LED chips 303 capable of emitting antimicrobial light. White light is made by LEDs in one of two ways. A blue LED with a phosphor coating converts the blue light to white light by fluorescence. Combining red, blue, and green LEDs also produces white light by varying intensities of the individual red, blue, and green chips. Red light may be characterized as visible light between 600 nm and 750 nm in wavelength. Blue light is generally between 425 and 500 nm in wavelength. While green light is generally between 500-575 nm. Wavelengths of light known as UVA have shown to have antimicrobial properties and lie in the 315-400 nm range. UVB light, 280-315 nm, and UVC, 100-280 nm, also may have antimicrobial properties but tend to be more harmful to human skin.

Figure 4:
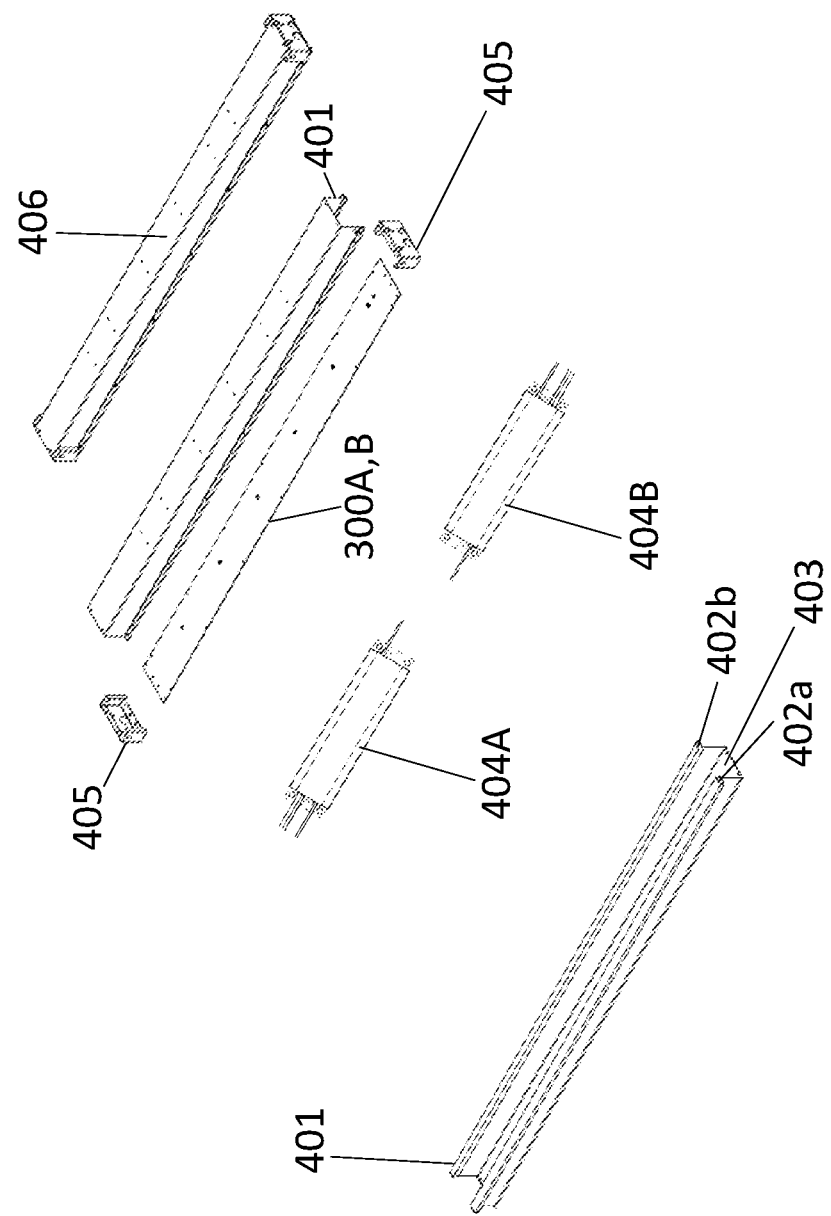
FIG. 4 illustrates formation of a LED light bar of the present disclosure.

As designed in FIG. 3, when power is delivered to the LED chips, a large amount of heat is being created by these chips. By attaching PCB arrays to heat sinks, generally metal structures that allow heat transfer to ambient or circulating air. Aluminum tends to be a good heat sink metal but others such as copper, or other heat conductive metals or materials may be used as well. FIG. 4 illustrates how a PCB array 300A,B may be fitted to a heat sink structure 401 to form an LED grow light bar 406.

As shown in FIG. 4, the PCB array 300A,B, of FIG. 3 can be attached to a heat sink housing 401. A long u-shaped heat sink 401 includes grooves 402a,b to receive the PCB array 300A,B. The trench 403 facilitates cooling as air may pass therethrough. Drivers 404 that supply power to the PCB array 300A,B, may be fitted inside or outside the heat sink housing 401. To assemble a LED grow light bar 406, the PCB array 300A,B is slid into the grooves 402a,b of the housing 401 and fixed with screws, pins, or clamps (not shown). The contact between the edges of the PCB array 300A,B and the groove 402a,b metal allows more efficient cooling as heat is directly transferred to the housing 401. End caps 405 may be fitted on the ends of the housing 401 to form a LED grow light bar 406, here shown from above with PCB array 300A,B facing down or away from the page.

Figure 6:
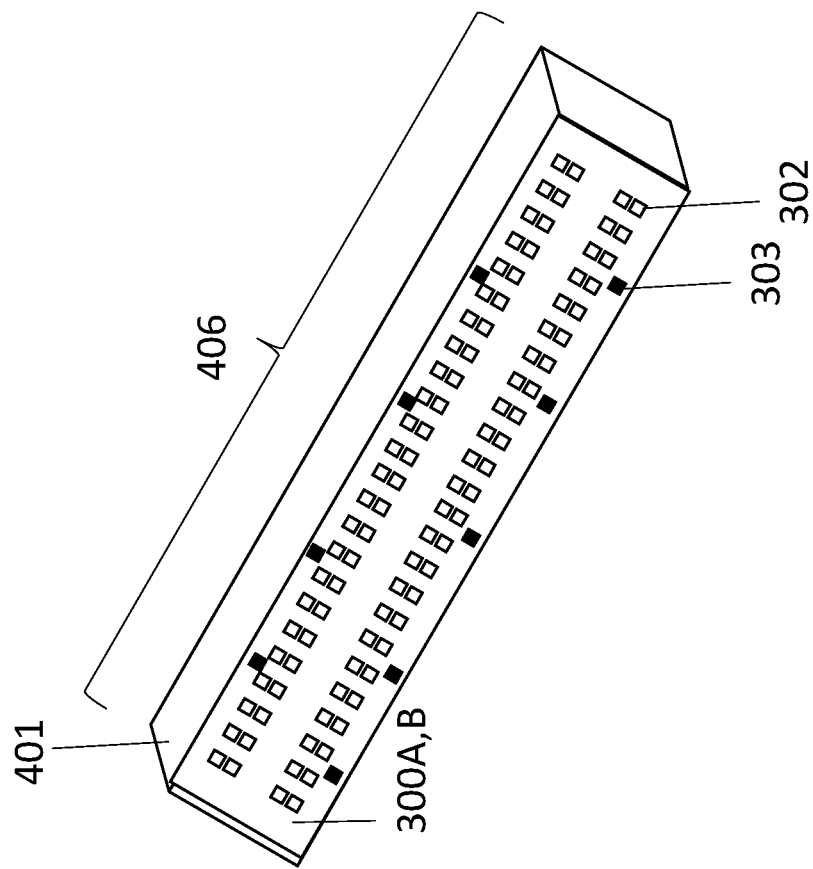
FIG. 6 is a bottom view of a LED light bar of the present disclosure.
Figure 5:
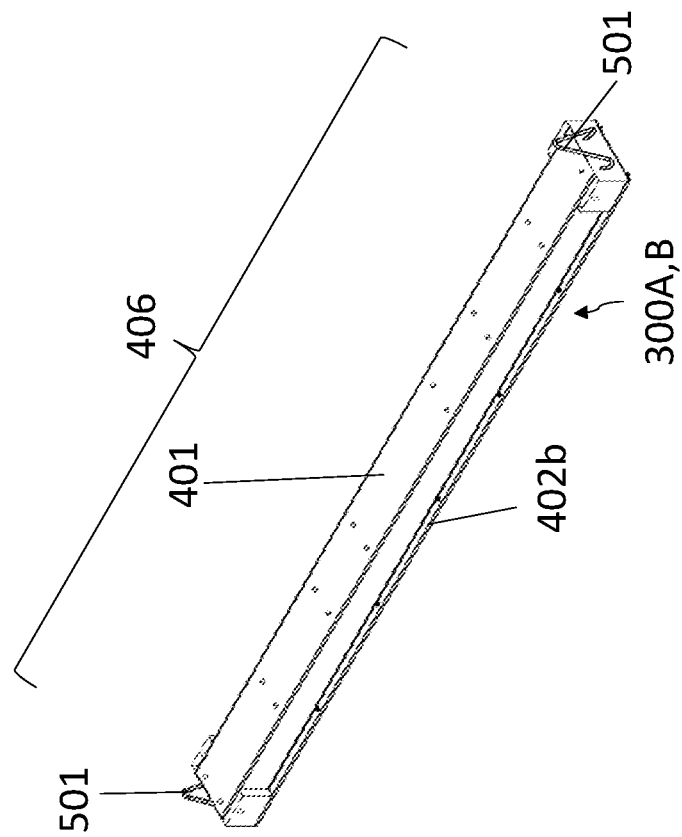
FIG. 5 is a top view of a LED light bar of the present disclosure.

FIG. 5 illustrates a LED grow light bar 406 including PCB array 300A,B, facing away from the page, and heat sink housing 401 with grooves 402b holding the PCB array 300A,B (not in view) of the present disclosure fitted with hanging brackets 501. As indicated above, the drivers may be mounted on the inside surface of the housing 401. FIG. 6 illustrates a generic grow light bar 406 as it would appear from the bottom or PCB array 300A,B having photosynthetic LED chips 302 and antimicrobial LED chips 303, with heat sink housing 401.

Figure 7:
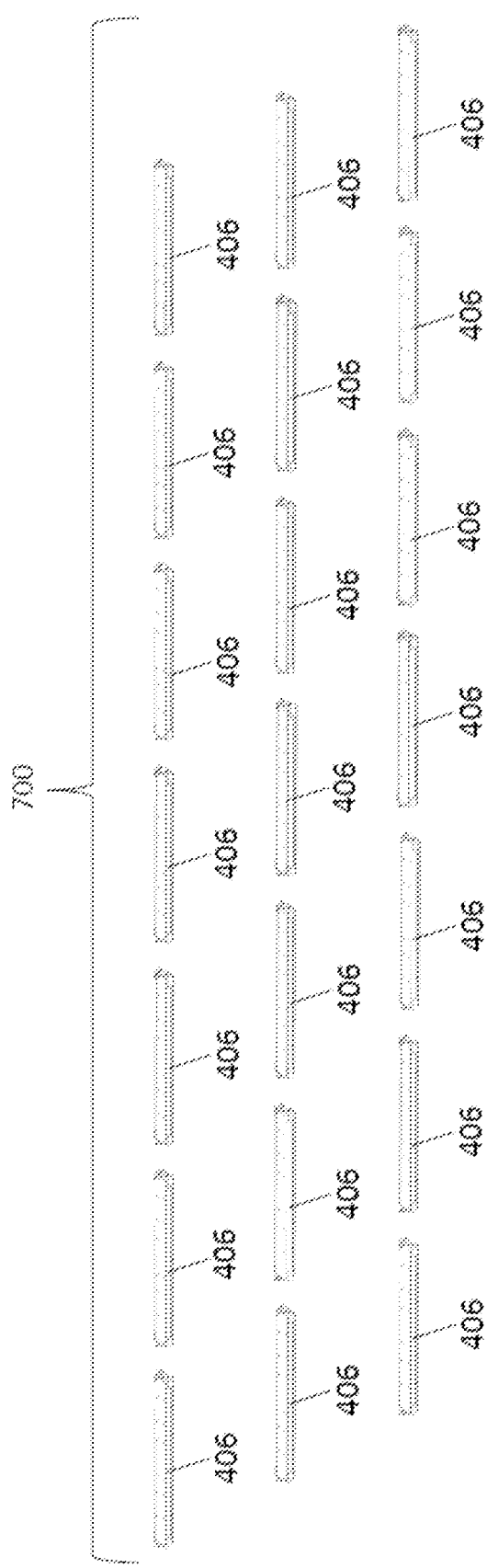
FIG. 7 illustrates one embodiment of an example LED light array of the present disclosure.

FIG. 7 depicts multiples of LED grow light bars 406 arranged in an array 700 as if they were hanging over plants in an indoor growing facility or greenhouse. Multiple configurations are possible. These grow lights may be at least one foot in length, or at least two feet in length, or at least 4 feet in length, or at least five feet in length, or at least six feet in length or more. Further, other arrangements are possible, some of which are described in the below examples.

A plant canopy is the top most leaf surface area that shades leaves and branches below. For the plant to be most efficient all of the photosynthetic surfaces should receive as much appropriate light as possible. Research, as shown in cited publications #1-5 listed below, shows that pulsed lighting increases light below the plant canopy. Further, Emerson and Chalmers (Refs. #10-11) found the sharp decline in the quantum yield of photosynthesis beyond 680 nm can be brought to full efficiency by simultaneously providing shorter wavelengths of light. They found that the effect of two superimposed beams of light on the rate of photosynthesis exceeds the sum effects of both beams of light used separately with the photosynthesis enhancement referred to as Emerson Effect.

EXAMPLES

Example 1

Figure 8:
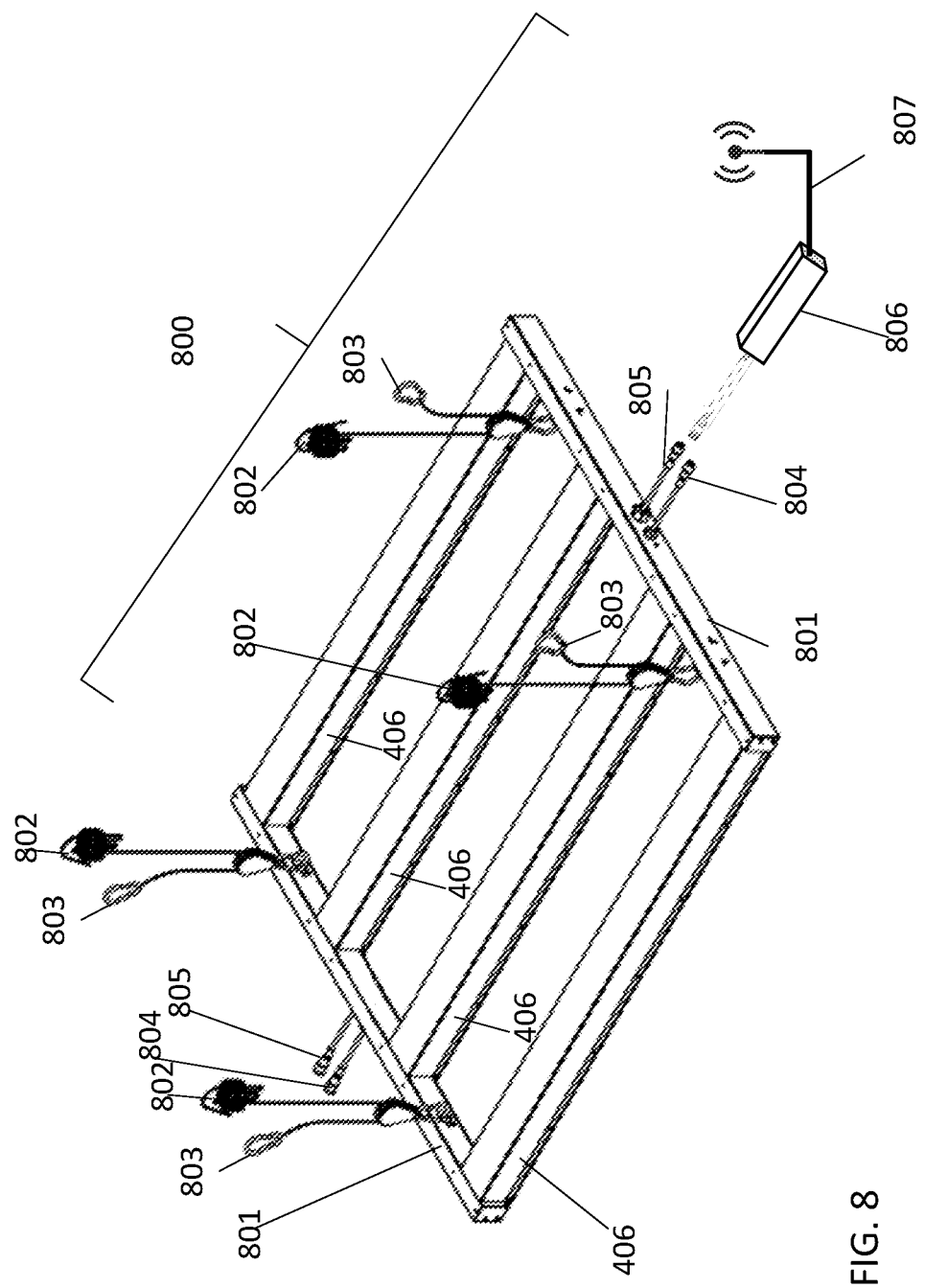
FIG. 8 illustrates an example LED light array of the present disclosure.

FIG. 8 depicts one example of a LED grow light array 800 of the present disclosure. To construct this LED grow light array, four LED grow light bars 406 are fitted to a pair of rectangular supports 801. The LED grow light bars 406 were connected at approximately equal distance from one another via the frame supports 801 which also house electrical wiring 804, 805 to connect the driver(s) (not shown) to a power source (not shown). A microprocessor/dimming processor 806 was connected to control power to the driver (not shown). The microprocessor 806 was fitted with a wireless receiver 807 to receive signal via WI-FI internet connection such that it may be sent a program with which to control power to the driver. Alternately the microprocessor may be connected via wired connection to receive the program for the LED drivers. The program, which may be called a lighting program, may be stored on a memory module on a remote or wired computing device and created via mobile application or software. The fixture dimension was approximately 4 ft by 4 ft. Power receptacle is a male type 804 that accepts power from circuit breaker and another receptacle is a female type 805 provides power to another LED grow light fixture 800 allowing daisy chain connection. A daisy chain connection connects the LED grow light bars 406 and/or multiple LED grow light arrays 800 in a series, thereby reducing wiring requirements. Hooks 802,803 are ratchet type of adjustable hanging hooks, but may be comprised of other type of hanging hardware including pulleys and hooks.

Figure 9:
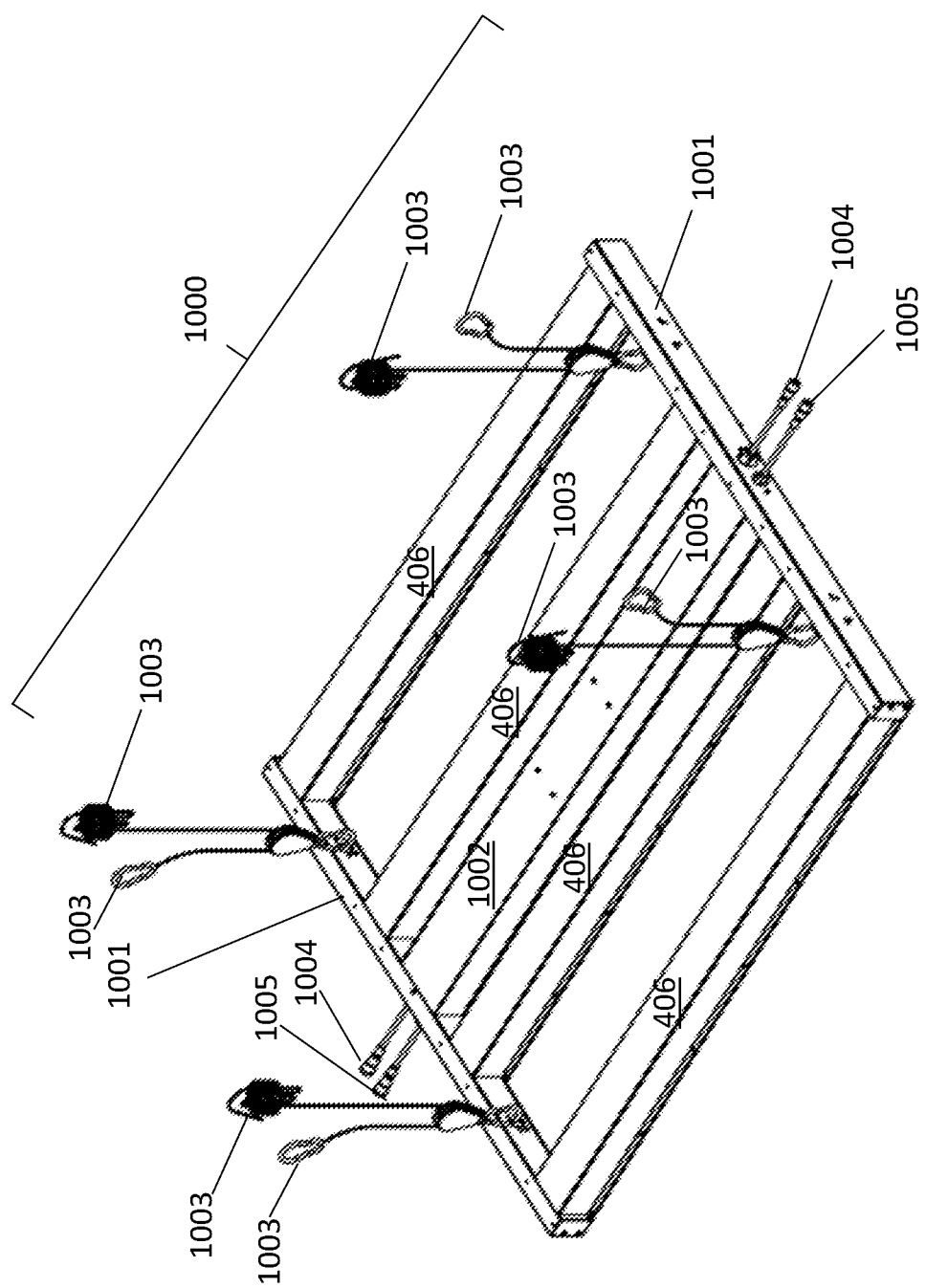
FIG. 9 illustrates an example LED light array of the present disclosure.

FIG. 9 illustrates a second arrangement of a 4-bar light bar 406 LED array 1000 built on a frame 1001 wherein the light bars 406 were spaced approximately equal distance from one another. The middle housing 1002 contains the LED drivers and microprocessor (not shown). Ratchet type adjustable hanging hooks 1003 connect the LED array 1000 to supports. Male type 1004 and female type 1005 power connectors supply power to the array 1000 and to other arrays in the series if present (not shown).

Figure 10:
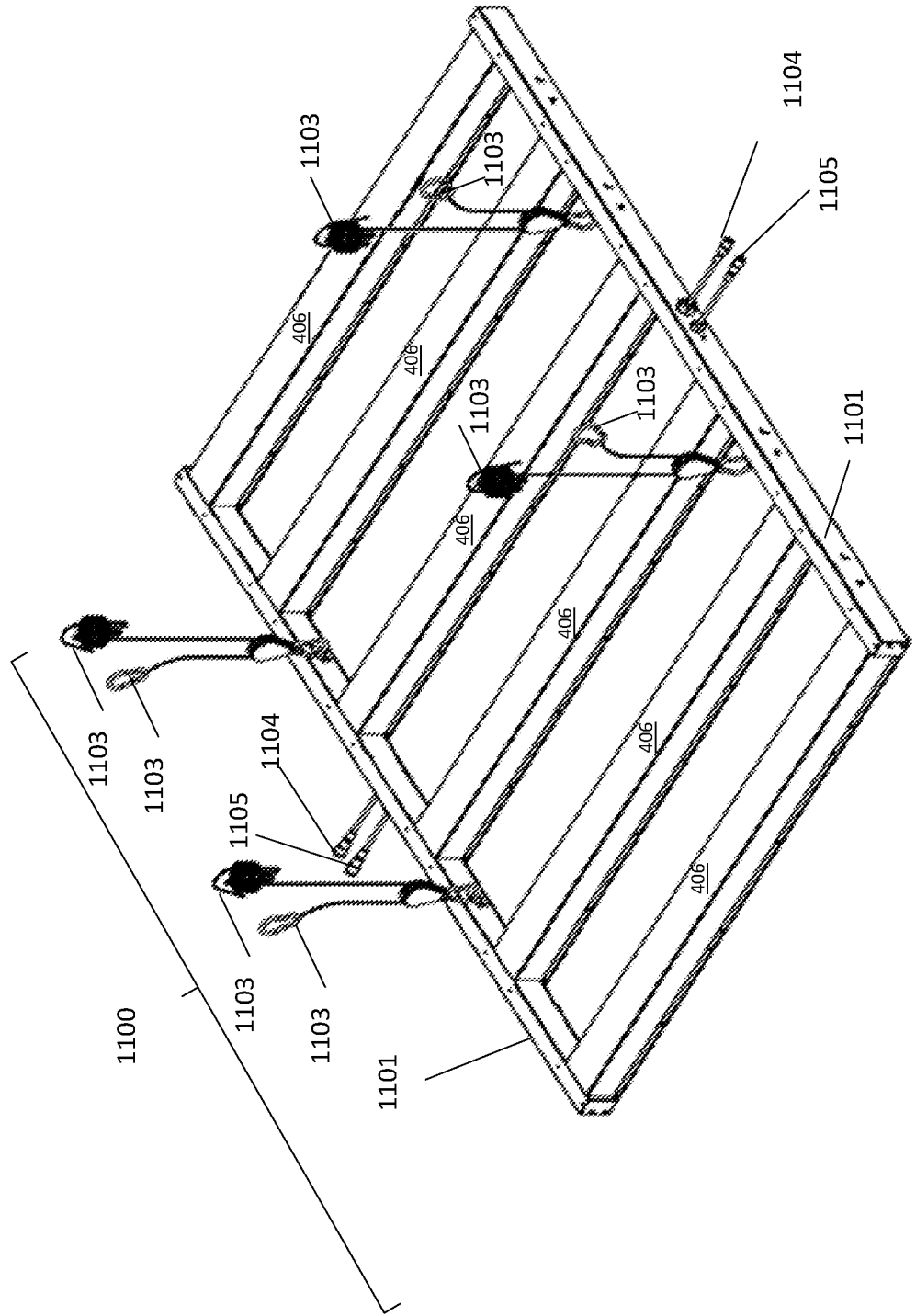
FIG. 10 illustrates an example LED light array of the present disclosure.

FIG. 10 is another arrangement of an LED light array 1100 of the present disclosure. With the same footprint as the FIG. 8 light array, the FIG. 11 array 1100 features six light bars 406 spaced over the four foot span instead of four bars of FIG. 8. Power to each light bar may be decreased to 100 W to achieve the same 600 W total energy usage of a four bar array of FIG. 8 that uses 150 W per bar. Alternately the wattage to each bar 406 may be reduced more, for instance, to 75 W or less. If lower power is used for each, for instance 75 W or less, it may reduce heat sink requirement saving cost of manufacture of the light array. As in FIG. 8, racket type hanging hooks 1103 connect the array 1100 to a support above. Male and female type power connectors 1104,1105 supply power to the driver (not shown) and/or another array in the series (not shown). As with the arrays described above in FIG. 8 and FIG. 9 800, 1000 a wired or wireless microprocessor controls the driver with a lighting program.

Figure 11:
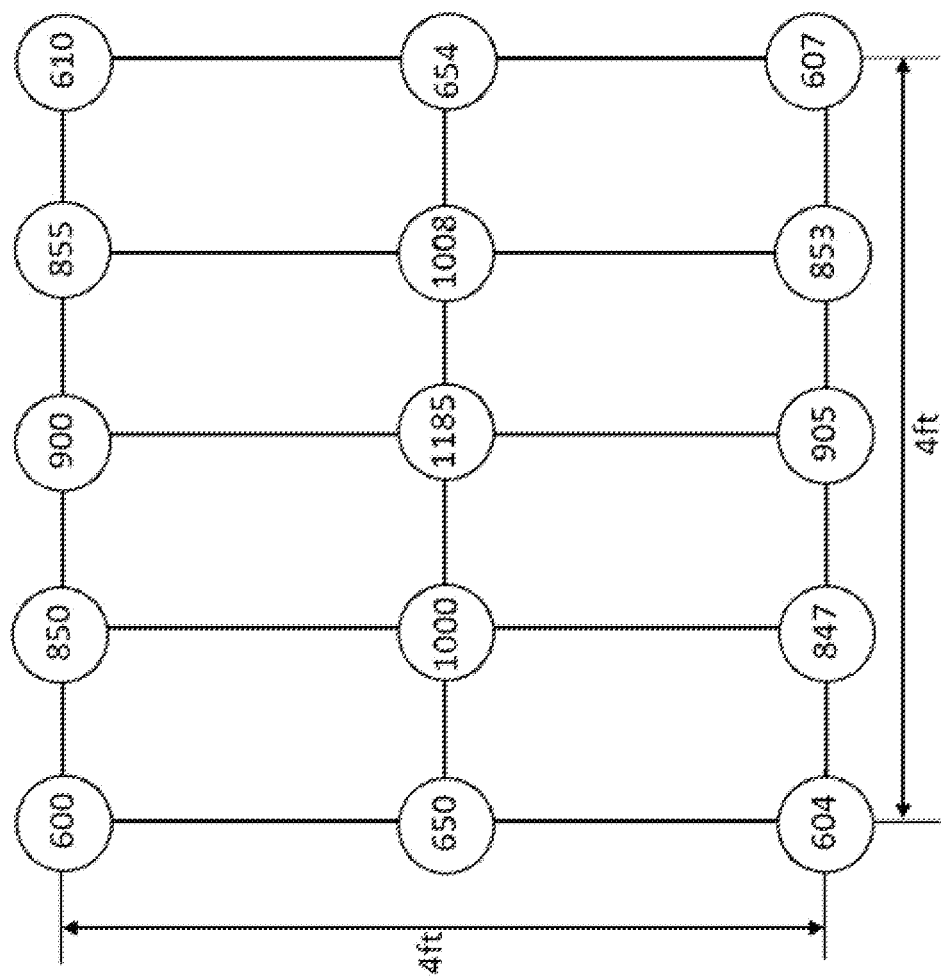
FIG. 11 illustrates PPFD data generated by the LED light array of FIG. 8.

In this example, LED energy in each LED bar 406 of FIG. 8 was set to 150 W, for total energy use of 600 W. PPFD was assessed over the 4 ft by 4 ft area as indicated in FIG. 11. As above, readings were taken 1 foot below array 1 foot apart. As is shown in FIG. 11 with 150 W delivered to each bar, FIG. 8, 406, PPFD ranges from about 900-1200 W in the center and around 600 W on the edges of the sampling or grow area. This can be contrasted to 1800 PPFD in the center for the prior art quantum array (FIGS. 1-2) and about 60-200 PPFD at two feet from center. The present example LED array FIG. 8, 800 reduces stationary hot spots in the center, spreads light more evenly, and improves light at edges of growing area.

As defined above, photosynthetic photon flux density (PPFD) is the amount of photosynthetically active photons (400-700 nm) hitting a surface per unit area per unit time. PPFD is reported in units of μmol per $m^2$ per second (s) or μmol/$m^2$/s of photons. Optimal growing conditions vary by plant but generally range from 50 PPFD when the plant is small and in the vegetative growth phase, to 500 PPFD, during the flowering and fruit producing state up to 1200 PPFD for some applications. In some rare cases with hearty plant types and carefully controlled watering a PPFD of 1800 or more may be used.

Example 2

Figure 12:
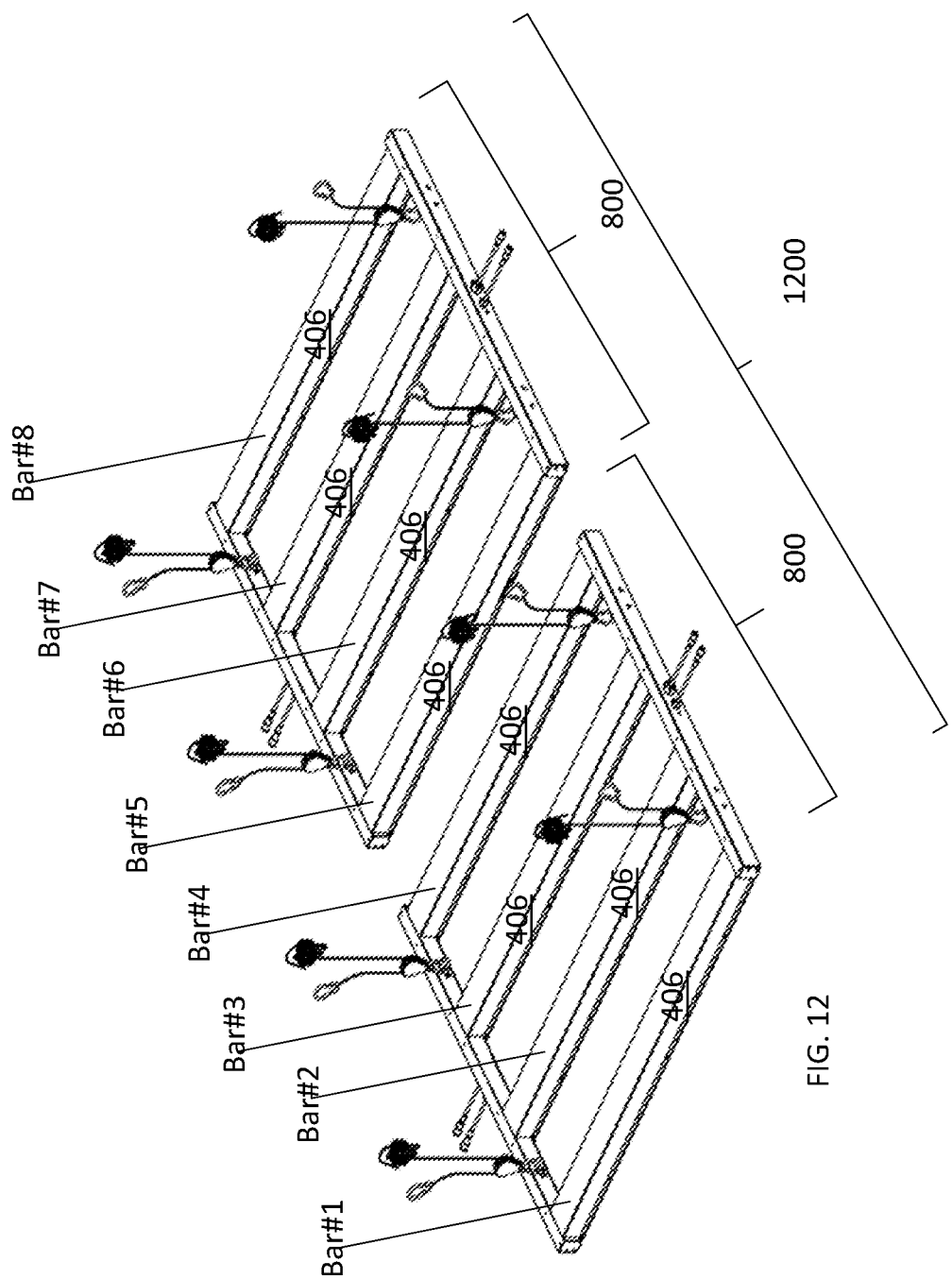
FIG. 12 illustrates an example LED light array of the present disclosure.
Figure 13:
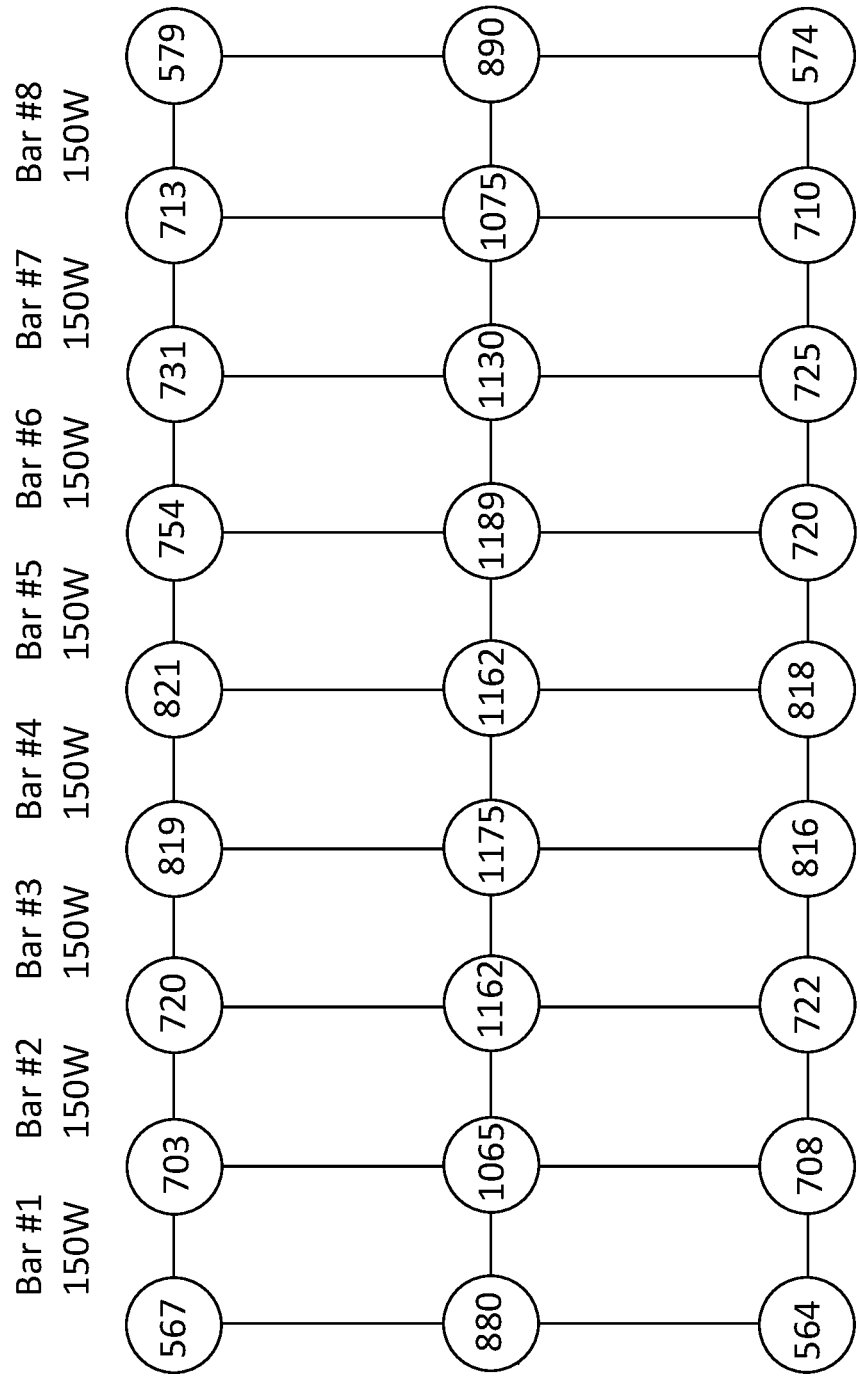
FIGS. 13-16 illustrates PPFD data generated by the LED light array of FIG. 12.

FIG. 12 illustrates another embodiment of an LED light array of the present disclosure. The LED light array 1200 consists of two, four bar arrays as specified in FIG. 8, 800 with all accompanying hardware, driver, and microprocessors. The LED light array 1200 creates an approximately eight foot by four foot array with bars 406 spaced evenly over the area. FIG. 13 illustrates PPFD data for the light array of FIG. 12, 1200. For this example, each bar received a feed of 150 W for a total of 1200 W. As above, readings were taken 1 foot below array 1 foot apart. As with the four bar array of FIG. 8, PPFD was roughly 1200 in the center and reduced to around 600 on the edges of the area, representing a loss of one-half PPFD as compared to thirty times loss for the prior art device of FIG. 1B. This more approximates target PPFD range of 500 to 1200.

Example 3

Figure 14:
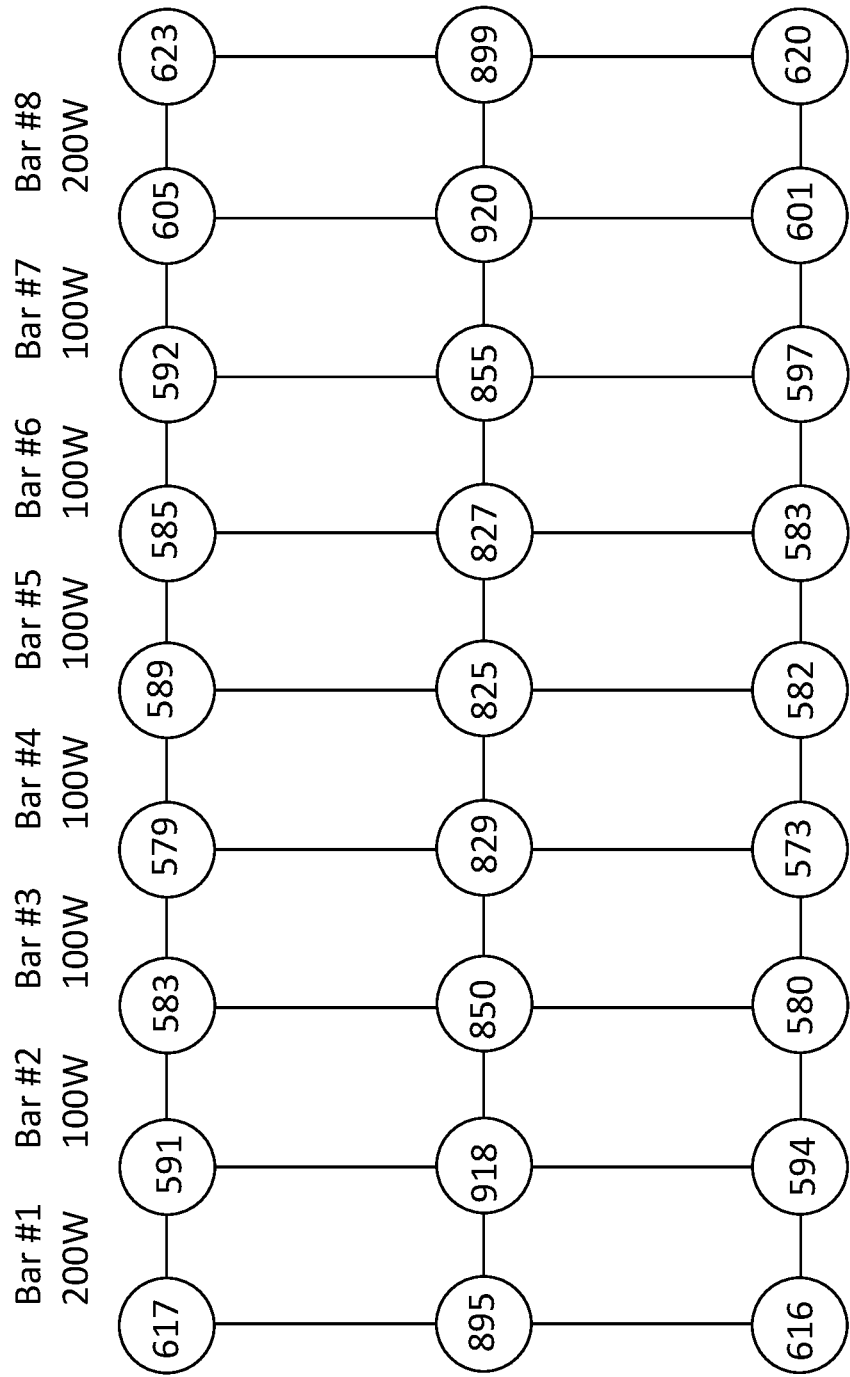

To increase light or PPFD at the edges of the growing area, light to the outer bars of the LED array of FIG. 12, 1200 was increased by increasing power supplied to the outer bars, for example Bar #1 and #8 as illustrated in FIG. 14. Power at 200 W was supplied to Bar #1 and #8, while only 100 W was supplied to inner Bars #2-6 for a total of 1000 W. As for FIG. 13, readings were taken 1 foot below array 1 foot apart. FIG. 14 illustrates PPFD data generated being around 800-900 PPFD in the center and 580-620 PPFD at the edges, achieving more uniform lighting over the entire 8 foot array as compared to the FIG. 13 lighting program and significantly more as compared to the prior art device of FIG. 1B.

Example 4

Figure 15:
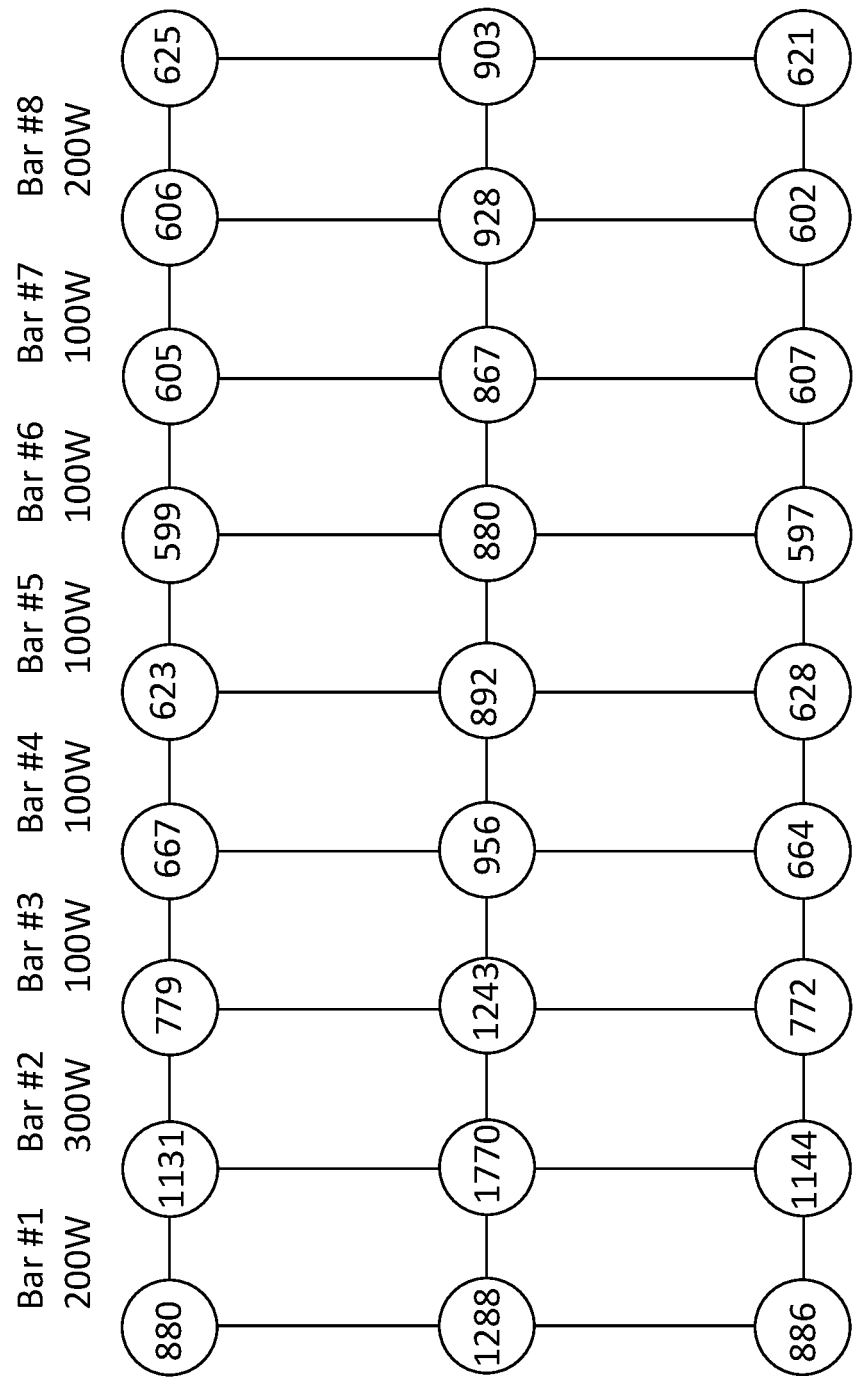

To increase light delivery below the plant canopy aim, we created example lighting programs that deliver increased amounts of light to certain areas for a given period of time by increasing and decreasing power to individual bars. To illustrate the effectiveness, wattage to each bar, #1-8 was set as follows: Bar #1 and #8 received 200 W and Bar #2-7 100 W each. Thereafter, Bar #2 received 200 W increased energy as shown in FIG. 15, for a total of 1200 W. As above, readings were taken 1 foot below array 1 foot apart. FIG. 15 shows that PPFD increased under the area of BAR #2 provided 300 W and PPFD was higher in adjoining spaces. Since light is additive crossover between Bars #1, #3, #4 and even #5 and #6, light increased in those areas. This proved increasing one bar's wattage for a short period of time, can help increase light in a particular area.

Figure 16:
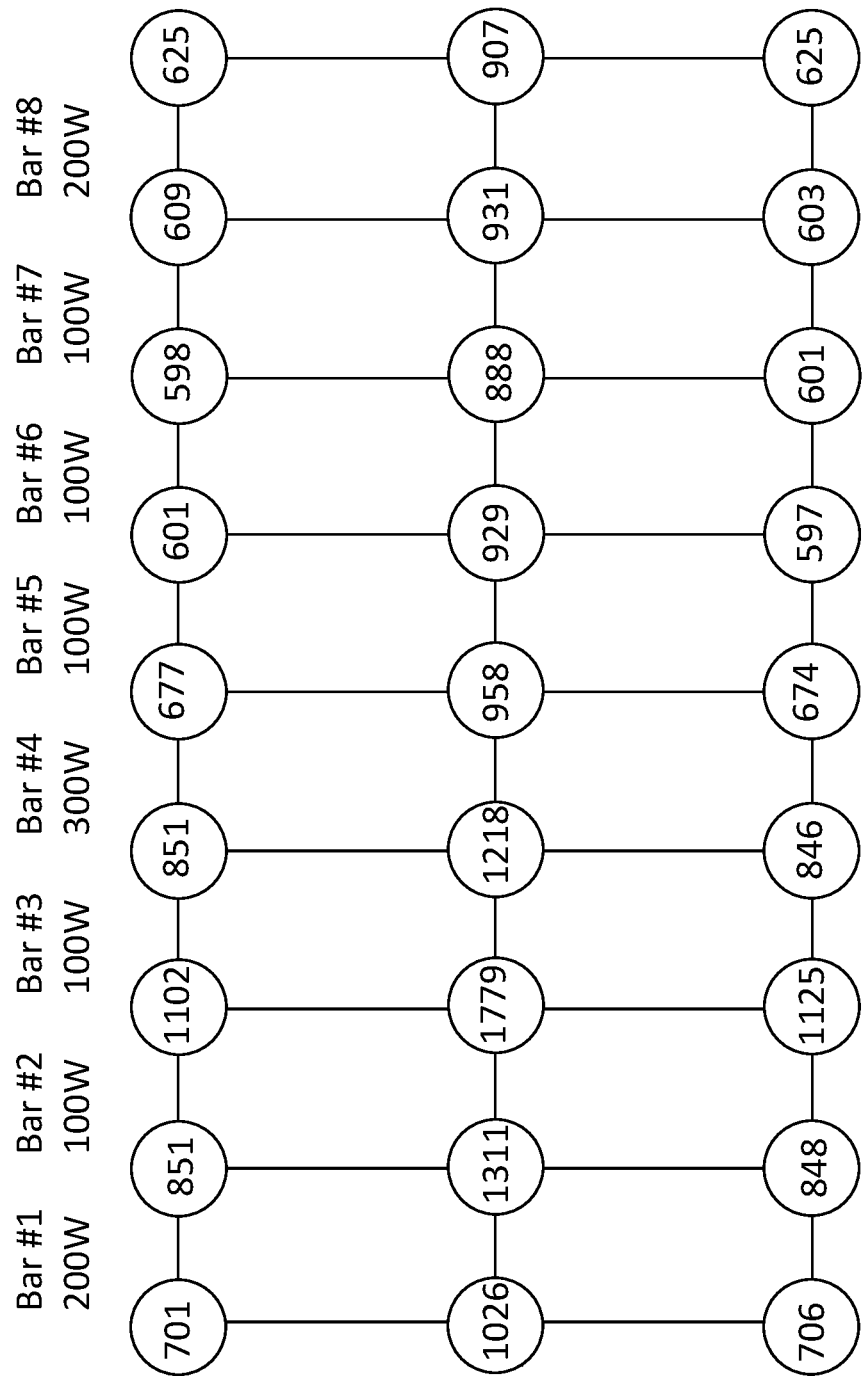

FIG. 16 illustrates what happens when the 200 W increased energy is moved to Bar #3 and Bar #2 is cycled back to 100 W. Wattage was set to each bar as follows: Bar #1 and #8 received 200 W, Bar #2-7 100 W and Bar #3 300 W as shown in FIG. 16, for a total of 1200 W. As for FIG. 15 example, FIG. 16 PPFD data illustrates that light under the bar and adjoint areas increased.

As the data shows, uniformity of lighting and increase in light below the plant canopy can be reached using comparable to even less energy by providing different amounts of energy to each light bar. Improved light uniformity and deeper light penetration with pulsing were hypothesized to increase amount of photosynthesis in plants resulting in greater crop yields. In order to improve lighting while keeping energy usage low, the following lighting programs examples were developed.

TABLE 1

Lighting Program 1-8 Bar Array as in FIG. 12. The initial power to each bar was set at 150 W and then changed in the following manner:, Bar #1 and #8 set to 200 W and Bar #2-7 set to 100 W each. Each light moving cycle consists of 6 identical sequential step energy increase in interior bars. One complete cycle is shown. The cycle may repeat as is or in reverse.

| Bar | Initial Power (W) | Cycle | Step 1 (W) | Step 2 (W) | Step 3 (W) | Step 4 (W) | Step 5 (W) | Step 6 (W) |
|---|---|---|---|---|---|---|---|---|
| #1 | 150 | 1 | 200 | 200 | 200 | 200 | 200 | 200 |
| #2 | 150 | 1 | 100 + 100 | 100 | 100 | 100 | 100 | 100 |
| #3 | 150 | 1 | 100 | 100 + 100 | 100 | 100 | 100 | 100 |
| #4 | 150 | 1 | 100 | 100 | 100 + 100 | 100 | 100 | 100 |
| #5 | 150 | 1 | 100 | 100 | 100 | 100 + 100 | 100 | 100 |
| #6 | 150 | 1 | 100 | 100 | 100 | 100 | 100 + 100 | 100 |
| #7 | 150 | 1 | 100 | 100 | 100 | 100 | 100 | 100 + 100 |
| #8 | 150 | 1 | 200 | 200 | 200 | 200 | 200 | 200 |
| Total | 1200 | 1 | 1100 | 1100 | 1100 | 1100 | 1100 | 1100 |

TABLE 2

Lighting Program 1-8 Bar Array as in FIG. 12. The initial power of 150 W to each bar was changed in the following manner, Bar #1 and #8 set to 200 W and Bar #2-7 set to 100 W each. Each cycle consists of 6 identical sequential 100 W photosynthetic step energy increase with 50 W antimicrobial light in interior bars. Duration of photosynthetic step energy and antimicrobial light is 2:1. One complete cycle is shown. The cycle may repeat as is or in reverse.

| Bar | Initial (W) | Cycle | Step 1 (W) | Step 2 (W) | Step 3 (W) | Step 4 (W) | Step 5 (W) | Step 6 (W) |
|---|---|---|---|---|---|---|---|---|
| #1 | 150 | 1 | 200 + 50 × 0.5 | 200 | 200 | 200 | 200 | 200 |

TABLE 2-continued

Lighting Program 1-8 Bar Array as in FIG. 12. The initial power of 150 W to each bar was changed in the following manner, Bar #1 and #8 set to 200 W and Bar #2-7 set to 100 W each. Each cycle consists of 6 identical sequential 100 W photosynthetic step energy increase with 50 W antimicrobial light in interior bars. Duration of photosynthetic step energy and antimicrobial light is 2:1. One complete cycle is shown. The cycle may repeat as is or in reverse.

| Bar | Initial (W) | Cycle | Step 1 (W) | Step 2 (W) | Step 3 (W) | Step 4 (W) | Step 5 (W) | Step 6 (W) |
|---|---|---|---|---|---|---|---|---|
| #2 | 150 | 1 | 100 + 100 + 50 × 0.5 | 100 | 100 | 100 | 100 | 100 |
| #3 | 50 | 1 | 100 | 100 + 100 + 50 × 0.5 | 100 | 100 | 100 | 100 |
| #4 | 150 | 1 | 100 | 100 | 100 + 100 + 50 × 0.5 | 100 | 100 | 100 |
| #5 | 150 | 1 | 100 | 100 | 100 | 100 + 100 + 50 × 0.5 | 100 | 100 |
| #6 | 150 | 1 | 100 | 100 | 100 | 100 | 100 + 100 + 50 × 0.5 | 100 |
| #7 | 150 | 1 | 100 | 100 | 100 | 100 | 100 | 100 + 100 + 50 × 0.5 |
| #8 | 150 | 1 | 200 | 200 | 200 | 200 | 200 | 200 + 50 × 0.5 |
| Tot | 1200 | 1 | 1150 | 1125 | 1125 | 1125 | 1125 | 1150 |

TABLE 3

Lighting Program 1-8 Bar Array as in FIG. 12. Initial power of 150 W to each bar was changed in the following manner: Bar #1 and #8 set to 200 W and Bar #2-7 set to 100 W each. Each cycle consists of 6 identical sequential 100 W photosynthetic step energy increase with 50 W antimicrobial light in interior bars, however, light sweeps from Bar #2 to Bar #4 and from Bar #7 to Bar #5. Duration of photosynthetic step energy and antimicrobial light is 2:1. One complete cycle is shown. The cycle may repeat as is or in reverse.

| Bar | Initial (W) | Cycle | Step 1 (W) | Step 2 (W) | Step 3 (W) | Step 4 (W) | Step 5 (W) | Step 6 (W) |
|---|---|---|---|---|---|---|---|---|
| #1 | 150 | 1 | 200 + 50 × 0.5 | 200 | 200 | 200 | 200 | 200 |
| #2 | 150 | 1 | 100 + 100 + 50 × 0.5 | 100 | 100 | 100 | 100 | 100 |
| #3 | 150 | 1 | 100 | 100 + 100 + 50 × 0.5 | 100 | 100 | 100 | 100 |
| #4 | 150 | 1 | 100 | 100 | 100 + 100 + 50 × 0.5 | 100 | 100 | 100 |
| #5 | 150 | 1 | 100 | 100 | 100 | 100 | 100 + 100 + 50 × 0.5 | |
| #6 | 150 | 1 | 100 | 100 | 100 | 100 + 100 + 50 × 0.5 | 100 | |
| #7 | 150 | 1 | 100 | 100 | 100 | 100 + 100 + 50 × 0.5 | 100 | 100 |
| #8 | 150 | 1 | 200 | 200 | 200 | 200 + 50 × 0.5 | 200 | |
| Tot | 1200 | 1 | 1150 | 1125 | 1125 | 1150 | 1125 | 1125 |

TABLE 4

Lighting Program 1-8 Bar Array as in FIG. 12. Initial power of each bar of 150 W was changed in the following manner: Bar #1 and #8 set to 200 W and Bar #2-7 set to 100 W each. Each cycle consists of 6 identical sequential 50 W photosynthetic step energy increase with 50 W antimicrobial light in interior bars, however, 50 W increased photosynthetic light is applied simultaneously to 2 interior bars next to each other. Duration of photosynthetic step energy and antimicrobial light is 2:1. One complete cycle is shown. The cycle may repeat as is or in reverse.

| Bar | Initial (W) | Cycle | Step 1 (W) | Step 2 (W) | Step 3 (W) | Step 4 (W) | Step 5 (W) | Step 6 (W) |
|---|---|---|---|---|---|---|---|---|
| #1 | 150 | 1 | 200 + 50 × 0.5 | 200 | 200 | 200 | 200 | 200 |
| #2 | 150 | 1 | 100 + 50 + 50 × 0.5 | 100 | 100 | 100 | 100 | 100 |
| #3 | 150 | 1 | 100 + 50 | 100 + 50 + 50 × 0.5 | 100 | 100 | 100 | 100 |
| #4 | 150 | 1 | 100 | 100 + 50 | 100 + 50 + 50 × 0.5 | 100 | 100 | 100 |
| #5 | 150 | 1 | 100 | 100 | 100 + 50 | 100 + 50 + 50 × 0.5 | 100 | 200 + 50 × 0.5 |
| #6 | 150 | 1 | 100 | 100 | 100 | 100 + 50 | 100 + 50 + 50 × 0.5 | 100 |
| #7 | 150 | 1 | 100 | 100 | 100 | | 100 + 50 | 100 + 50 + 50 × 0.5 |
| #8 | 150 | 1 | 200 | 200 | 200 | 200 | 200 | 200 + 50 × 0.5 |
| Tot | 1200 | 1 | 1150 | 1125 | 1125 | 1125 | 1125 | 1150 |

TABLE 5

Lighting Program 1-8 Bar Array as in FIG. 12. Initial power of 150 W to each bar was changed in the following manner: Bar #1 and #8 set to 200 W and Bar #2-7 set to 100 W each. Each cycle consists of 6 identical sequential 100 W white photosynthetic step energy increase with 50 W antimicrobial light in interior bars and 6 identical sequential 50 W 660 nm photosynthetic step energy increase with 50 W antimicrobial light in interior bars. Duration of photosynthetic step energy and antimicrobial light is 2:1. One complete cycle, 12 steps, is shown. The cycle may repeat as is or in reverse.

Table 5A: Step 1-6 with 100 W white photosynthetic light

| Bar | Initial (W) | Cycle | Step 1 (W) | Step 2 (W) | Step 3 (W) | Step 4 (W) | Step 5 (W) | Step 6 (W) |
|---|---|---|---|---|---|---|---|---|
| #1 | 150 | 1 | 200 + 50 × 0.5 | 200 | 200 | 200 | 200 | 200 |
| #2 | 150 | 1 | 100 + 100 + 50 × 0.5 | 100 | 100 | 100 | 100 | 100 |
| #3 | 150 | 1 | 100 | 100 + 100 + 50 × 0.5 | 100 | 100 | 100 | 100 |
| #4 | 150 | 1 | 100 | 100 | 100 + 100 + 50 × 0.5 | 100 | 100 | 100 |
| #5 | 150 | 1 | 100 | 100 | 100 | 100 + 100 + 50 × 0.5 | 100 | 100 |
| #6 | 150 | 1 | 100 | 100 | 100 | 100 | 100 + 100 + 50 × 0.5 | 100 |
| #7 | 150 | 1 | 100 | 100 | 100 | 100 | 100 | 100 + 100 + 50 × 0.5 |
| #8 | 150 | 1 | 200 | 200 | 200 | 200 | 200 | 200 + 50 × 0.5 |
| Tot | 1200 | 1 | 1150 | 1125 | 1125 | 1125 | 1125 | 1150 |

TABLE 5-continued

Lighting Program 1-8 Bar Array as in FIG. 12. Initial power of 150 W to
each bar was changed in the following manner: Bar #1 and #8 set to 200 W and Bar #2-7 set to 100
W each. Each cycle consists of 6 identical sequential 100 W white photosynthetic step energy
increase with 50 W antimicrobial light in interior bars and 6 identical sequential 50 W 660 nm
photosynthetic step energy increase with 50 W antimicrobial light in interior bars. Duration of
photosynthetic step energy and antimicrobial light is 2:1. One complete cycle, 12 steps, is shown.
The cycle may repeat as is or in reverse.

Table 5B: Step 7-12 with 50 W 660 nm photosynthetic light

| Bar | Initial (W) | Cycle | Step 7 (W) | Step 8 (W) | Step 9 (W) | Step 10 (W) | Step 11 (W) | Step 12 (W) |
|---|---|---|---|---|---|---|---|---|
| #1 | 150 | 1 | 200 + 50 × 0.5 | 200 | 200 | 200 | 200 | 200 |
| #2 | 150 | 1 | 100 + 50 + 50 × 0.5 | 100 | 100 | 100 | 100 | 100 |
| #3 | 150 | 1 | 100 | 100 + 50 + 50 × 0.5 | 100 | 100 | 100 | 100 |
| #4 | 150 | 1 | 100 | 100 | 100 + 50 + 50 × 0.5 | 100 | 100 | 100 |
| #5 | 150 | 1 | 100 | 100 | 100 | 100 + 50 + 50 × 0.5 | 100 | 100 |
| #6 | 150 | 1 | 100 | 100 | 100 | 100 | 100 + 50 + 50 × 0.5 | 100 |
| #7 | 150 | 1 | 100 | 100 | 100 | 100 | 100 | 100 + 50 + 50 × 0.5 |
| #8 | 150 | 1 | 200 | 200 | 200 | 200 | 200 | 200 + 50 × 0.5 |
| Tot | 1200 | 1 | 1100 | 1075 | 1075 | 1075 | 1075 | 1100 |

TABLE 6

Pulsed lighting is targeted for energy savings and improved photosynthetic as
well as antimicrobial activities. The lighting Program 1-8 Bar Array as in FIG. 12, initial 150 W
to each bar was changed. Bar #1 and #8 set to 200 W and Bar #2-7 set to 100 W each. Each cycle
consists of 6 identical sequential 100 W step energy increase with 60 W antimicrobial light in
interior bars. Antimicrobial light is pulsed 10 times, 50% on 50% off during half of the
photosynthetic step increase duration. Average antimicrobial light energy is 60 × 0.5 × 0.5 15 W.
One complete cycle is shown. The cycle may repeat as is or in reverse.

| Bar | Initial (W) | Cycle | Step 1 (W) | Step 2 (W) | Step 3 (W) | Step 4 (W) | Step 4 (W) | Step 5 (W) |
|---|---|---|---|---|---|---|---|---|
| #1 | 150 | 1 | 200 + 60 × .25 | 200 | 200 | 200 | 200 | 200 |
| #2 | 150 | 1 | 100 + 100 + 60 × .25 | 100 | 100 | 100 | 100 | 100 |
| #3 | 150 | 1 | 100 | 100 + 100 + 60 × .25 | 100 | 100 | 100 | 100 |
| #4 | 150 | 1 | 100 | 100 | 100 + 100 + 60 × .25 | 100 | 100 | 100 |
| #5 | 150 | 1 | 100 | 100 | 100 | 100 + 100 + 60 × .25 | 100 | 100 |
| #6 | 150 | 1 | 100 | 100 | 100 | 100 | 100 + 100 + 60 × .25 | 100 |
| #7 | 150 | 1 | 100 | 100 | 100 | 100 | 100 + 100 + 60 × .25 | |
| #8 | 150 | 1 | 200 | 200 | 200 | 200 | 200 + 60 × 0.25 | |
| Tot | 1200 | 1 | 1130 | 1115 | 1115 | 1115 | 1115 | 1130 |

TABLE 7

The lighting Program 1-8 Bar Array as in FIG. 12, initial 150 W to each bar was changed. Bar #1 and #8 set to 200 W and Bar #2-7 set to 100 W each. Each cycle consists of 6 identical sequential 200 W pulsed step energy increase with 60 W antimicrobial pulsed light in interior bars. Photosynthetic step energy pulsed 20 times, 50% on 50% off. Average Step energy is 200 × 0.5 equals to 100 W. Antimicrobial light is also pulsed 10 times, 50% on 50% off during half of the photosynthetic step increase duration. Average antimicrobial light energy is 60 × 0.5 × 0.5 equals to 15 W. One complete cycle is shown.

| Bar | Initial (W) | Cycle | Step 1 (W) | Step 2 (W) | Step 3 (W) | Step 4 (W) | Step 4 (W) | Step 5 (W) |
|---|---|---|---|---|---|---|---|---|
| #1 | 150 | 1 | 200 + 15 | 200 | 200 | 200 | 200 | 200 |
| #2 | 150 | 1 | 100 + 200 × 0.5 + 60 × .25 | 100 | 100 | 100 | 100 | 100 |
| #3 | 150 | 1 | 100 | 100 + 200 × 0.5 + 60 × .25 | 100 | 100 | 100 | 100 |
| #4 | 150 | 1 | 100 | 100 | 100 + 100 + 60 × .25 | 100 | 100 | 100 |
| #5 | 150 | 1 | 100 | 100 | 100 | 100 + 100 + 60 × .25 | 100 | 100 |
| #6 | 150 | 1 | 100 | 100 | 100 | 100 | 100 + 100 + 60 × .25 | 100 |
| #7 | 150 | 1 | 100 | 100 | 100 | 100 | 100 | 100 + 100 + 60 × .25 |
| #8 | 150 | 1 | 200 | 200 | 200 | 200 | 200 | 200 + 60 × 0.25 |
| Tot | 1200 | 1 | 1130 | 1115 | 1115 | 1115 | 1115 | 1130 |

Example 5: Photosynthetic LEDs

Different photosynthetic LED chips may be powered within the lighting program. For instance during a flowering period of the plants' grow cycle adding an additional red spectrum wavelength is beneficial. Therefore a photosynthetic LED chips producing specifically 660 nm wavelength light could be powered on each bar sequentially at least 10 watts, or at least 20 watts, or at least 30 watts, or at least 40 watts, or at least 50 watts, or more. Other wavelengths that may improve crop yield include 450 nm, 720 nm, and 385 nm. These could be applied to the bars in sequence first the 660 nm wavelength, then the 720 nm, then 385 nm chips with varying duration. The 660 nm may be applied for example for 20 seconds, 720 nm for lesser time, for example 8 seconds, and then the 390 nm for 5 seconds or less. Additionally light may be applied for as little as 0.05 s, or 1 s to as much as 60 seconds or more.

Example 6: Antimicrobial LEDs

Ultra-violet light has been shown to reduce growth of bacteria, fungi, and other detrimental plant pathogens as is indicated by cited publications #6-9. Therefore, we proposed different antimicrobial LED chips may be powered in a sequential sweeping manner within the lighting program. UV light has been shown to reduce microbial, including bacterial, mold, and fungus, growth on plants. Longer wavelength UV light, being UVA is safer for human skin, so wavelengths including 405 nm and 385 nm may be employed for example. However, since sequential sweeping limits stationary exposure time, therefore, other wavelengths may be used. At present UVA LEDs lower than 385 nm are very inefficient. Only 2 to 10 percent energy is converted into UV light. Therefore, by limiting the wattage in UV LEDs the use wavelengths lower than 385 nm for shorter duration of time in each light bar in sequence will not create problem to human. Further, by applying pulsed UV lights with 50% duty cycle, that is, on 50% and off 50% of the time allows to double UV intensity without increasing power consumption. For example at least 10 watts, or at least 20 watts, or at least 30 watts, or at least 40 watts, or at least 50 watts, or more may be applied. Durations of time may include as little as 0.00005 s, or 0.05 s, or 0.1 s, or 1 s, or 2 s, or 3 s, or 4 s, or 5 sec, 10 s, 20 s or more. These wattages may be applied by pulsing for instance on 1 s, off 1 s, on 1 s in a first bar, then the second, sequentially being powered on in each bar. There may be as many as two pulses, or three, or four, or more per light bar. The sweeping antimicrobial light in combination with sweeping increased white photosynthetic light may be used for treating packaged and unpackaged produce after harvesting.

Figure 17:
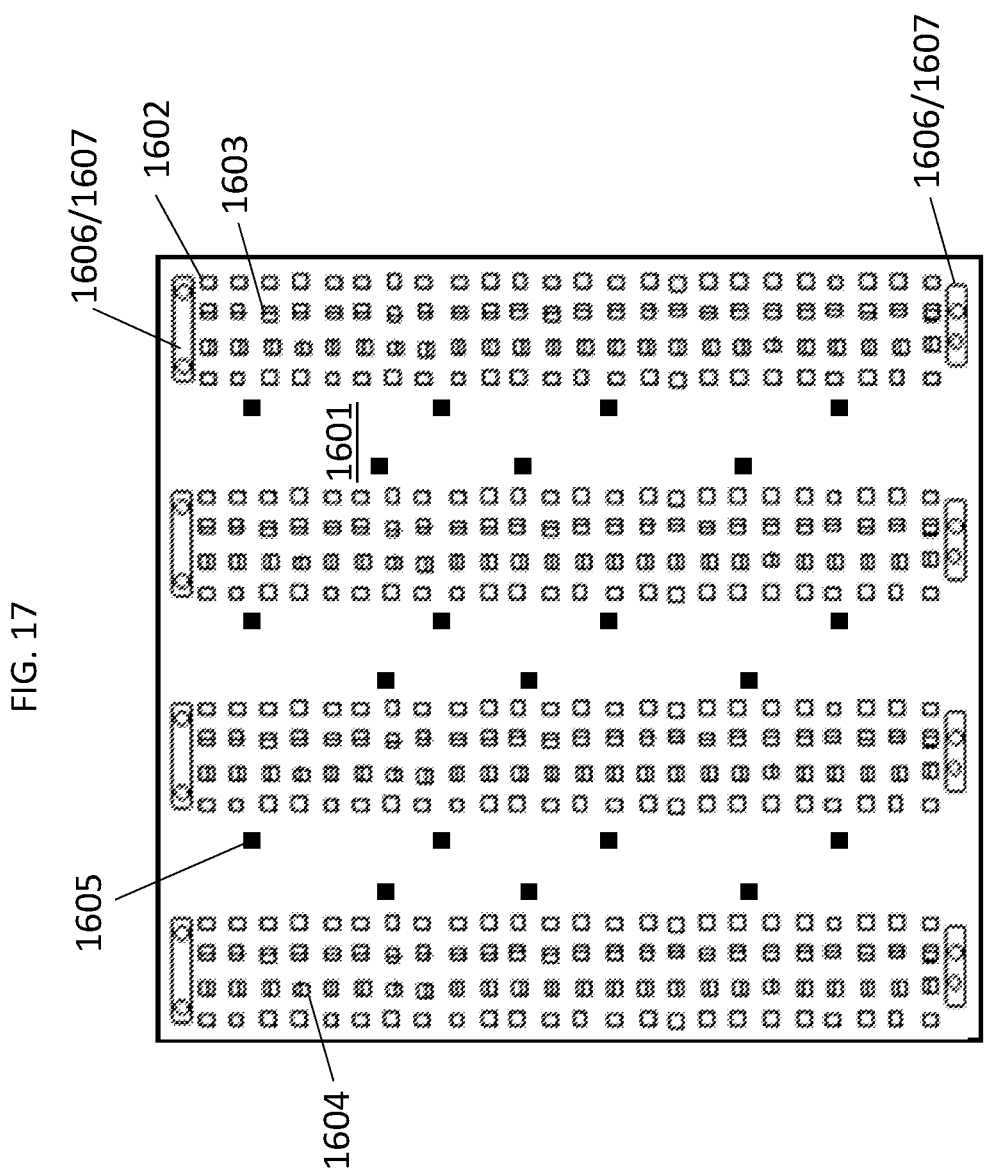
FIG. 17 illustrates an example LED light array of the present disclosure.

Further, LED chips that may be distributed among four different bars, as is shown in FIG. 8, 406, 800, or they may be fixed to a single PCB. In FIG. 17 for example, a larger PCB, 1601, which may be at least 4 ft wide, or at least 6 ft wide, or at least 8 ft wide, or more, may be fixed with rows of LED chips equivalent to the number of chips found on 4 individual bars FIG. 8, 406, 800. Several different LED chips may be employed for example those emitting white light 1602, represented by empty squares, red light at 660 nm 1603, represented by squares with vertical line, or far red of 720 nm 1604, represented by squares with horizontal lines, and antimicrobial LED chips 1605, represented by black squares, which may emit 405 nm or 385 nm, or other UV light. Associated circuitry and connectors 1606 would connect the chips to the controller (not shown). Hardware 1607 would be used for mounting to a heat sink and/or housing (not shown).

Figure 18:
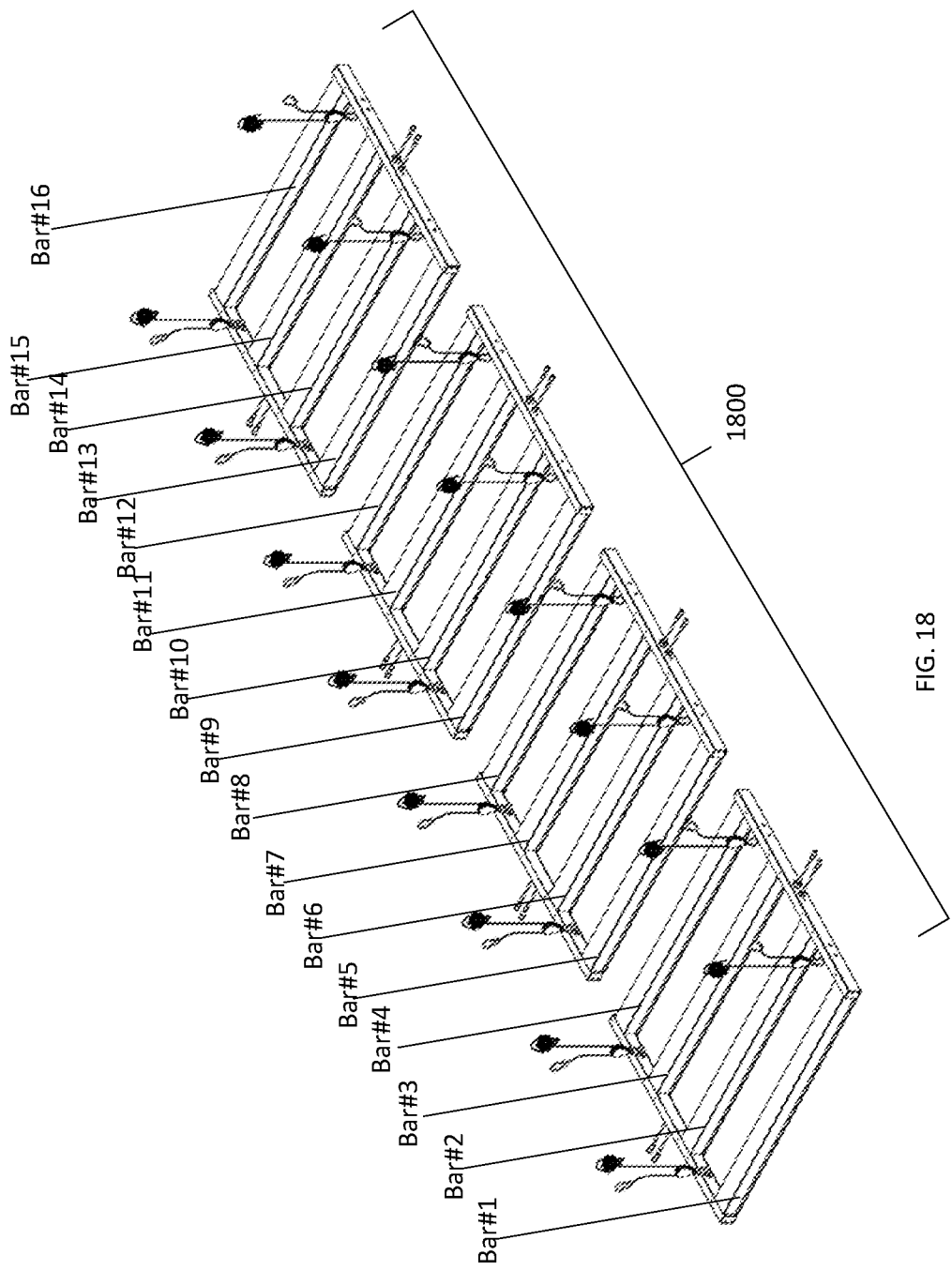
FIG. 18 illustrates another embodiment of an LED light array of the present disclosure.

Alternate arrangements for an LED grow array may include the following. As shown in FIG. 18, four 4-bar LED arrays 1800 may be arranged together and the lighting program designed to include supplying varying wattage sequentially, in ascending and/or descending order, over the sixteen bars.

Example 8

When growing plants from seed or clone, the plants will have different light requirements in different stages of growth. With programmable grow light arrays that are tailored to the needs of each individual stage, much energy can be saved. For instance if using a 150 W power feed to each light bar in a 4-bar array one would utilize 2400 W. However, with a tailored lighting program the following energy savings may be achieved as indicated in Table 8.

TABLE 8

Energy consumption data for tailored grow plan with 8, 4-bar arrays

| Growth phase | Duration (weeks) | Energy each first and last grow bar (W) | Energy each interior grow bar (W) | 20 s sequential increases to interior grow bars (W) | 5 sec sequential pulses anti-microbial light (W) | Total energy consumption per cycle (W) |
|---|---|---|---|---|---|---|
| Vegetative | 2 | 100 | 50 | 50 | 60 × 0.25 | 965 |
| Beginning to bloom | 2 | 150 | 100 | 50 | 60 × 0.25 | 1765 |
| Bloom to harvest | 4 | 200 | 100 | 200 | 60 × 0.25 | 2065 |

As seen in table 8, the average energy consumption over an eight weeks grow period is (965 W×2+1765 W×2+2065 W×4)/8 weeks=1690 W. Nominal power consumption of 4 four bar LED arrays is 4×600=2400 W, almost 30% energy savings versus tradition LED grow light methods. Further, PPFD data indicates increased uniformity and penetration of light across a growing area. Addition of antimicrobial LED chips reduces unwanted microbial growth further benefitting production.

Figure 19:
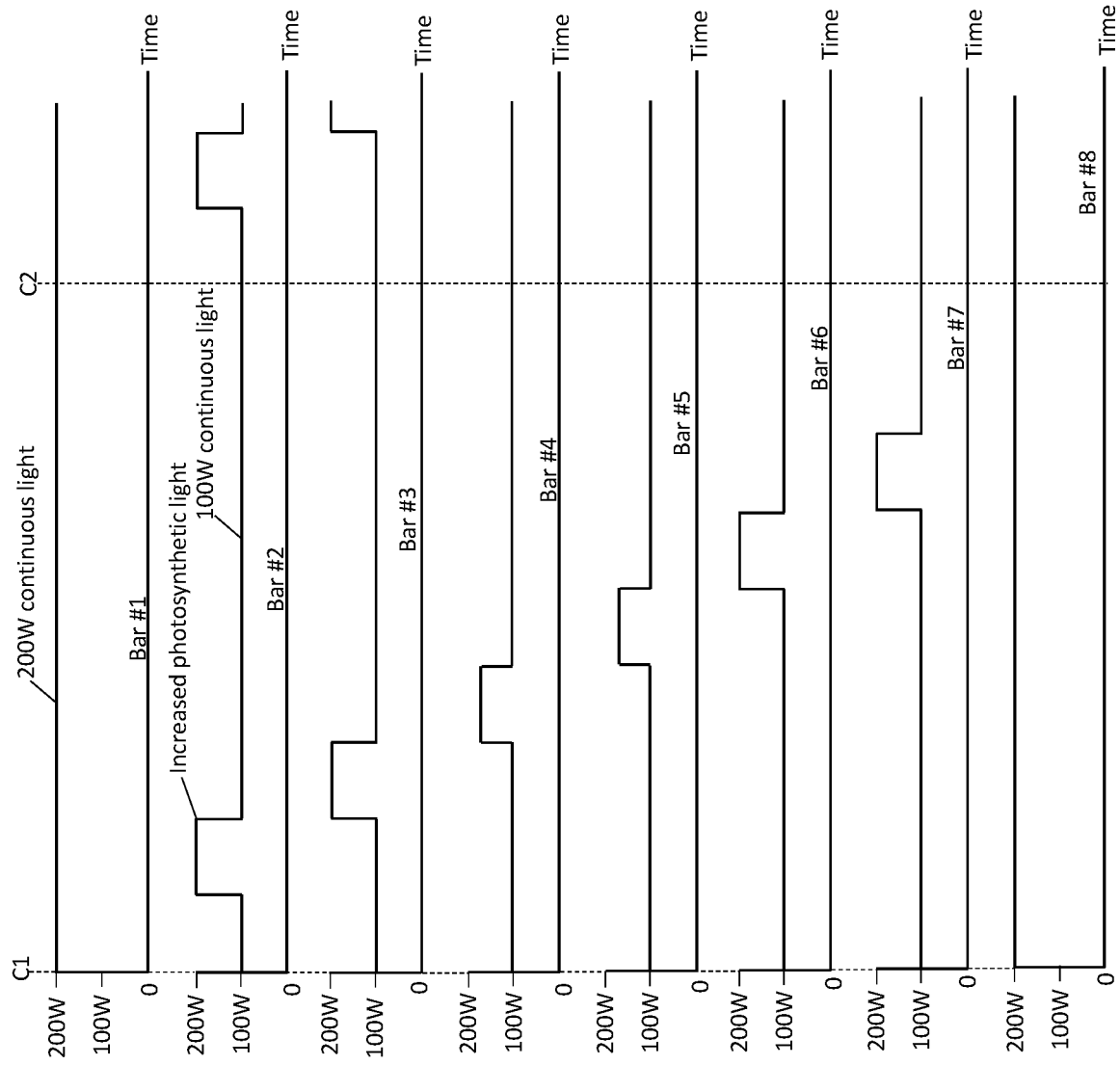
FIGS. 19-28 illustrate example lighting programs of the present disclosure.

FIG. 19 illustrates a growing program for a flowering phase plant where increased step energy is applied in an interior Bar one at a time without antibacterial light. Bar #1 and Bar #8 receive 200 W and Bar #2-#7 receive 100 W continuous power. Bar #2, Bar #3, Bar 6 and Bar #7 receive 100 W increased power, whereas, the middle Bars #4 and #5 receives less, 50 W increased power. Wattage is shown on the left. C1 and C2 indicating Cycle 1 and Cycle 2, repeating cycles of wattage change across 8 Bars as in the example LED Array of FIG. 12, 1200. Total energy consumption is approximately 1083 W.

Figure 20:
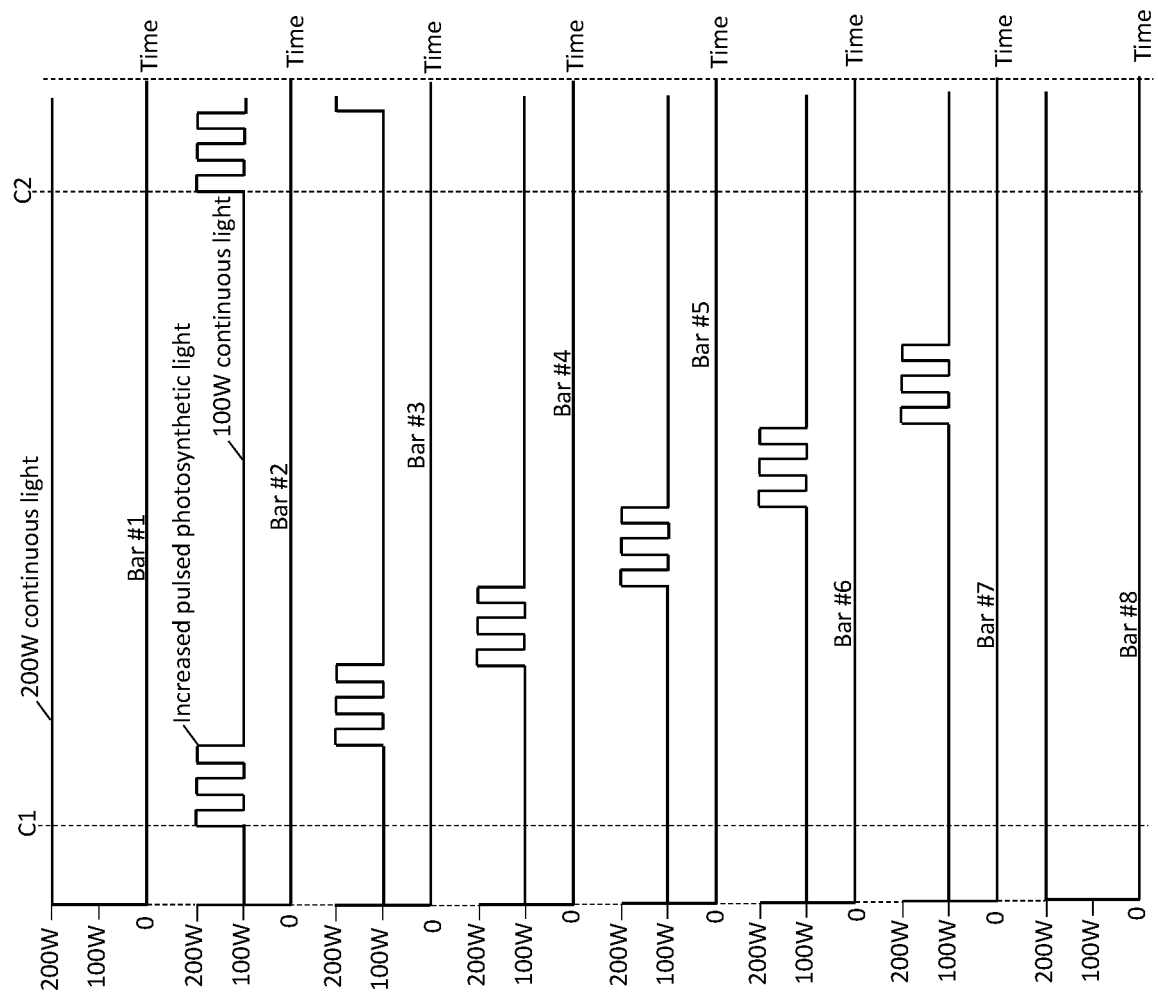

FIG. 20 illustrates a growing program for a flowering phase plant where increased pulsed step energy is applied in an interior Bar one at a time without antibacterial light. Bar #1 and Bar #8 receive 200 W and Bar #2-#7 receive 100 W continuous power. Bar #2-Bar #7 receive 100 W increased power. There are 3 pulses in increased energy with equal on and off time consuming approximately 33 W. Wattage is shown on the left. C1 and C2 indicating Cycle 1 and Cycle 2, repeating cycles of wattage change across 8 Bars as in the example LED Array of FIG. 12, 1200. Total energy consumption is approximately 1033 W.

Figure 21:
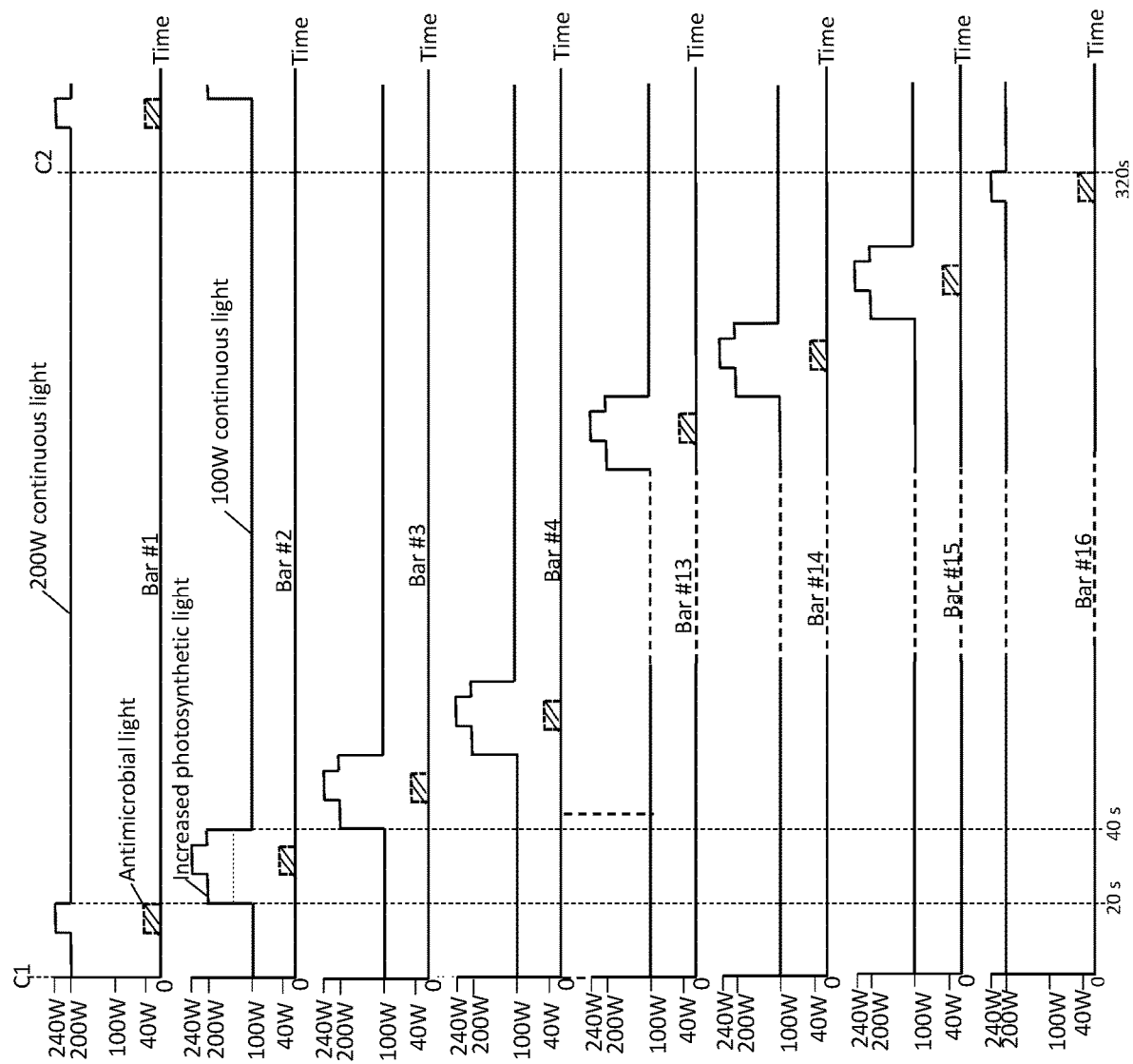

FIG. 21 illustrates a growing program for a flowering phase plant where increased step energy in an interior applied one at a time. The antibacterial light is applied in sequence superimposed on photosynthetic light. Wattage is shown on the left. C1 and C2 indicating Cycle 1 and Cycle 2, repeating cycles of wattage change across 16 Bars as in the example LED Array of FIG. 18, 1800. Bars #1-4 and #13-16 are shown for ease of example. Bars #5-12 would receive the same pattern of light in sequence. Sequences may repeat in ascending or descending order. Total power consumption, #1 and #16 bars 200 W each plus #3-#15 bars 100 W each plus 100 W increased photosynthetic energy plus 40 W antimicrobial light for 2:5 increased photosynthetic energy duration, is 1916 W.

Flowering phase requires eight or more hours of lighting daily. The growing program of FIG. 21 could be such that where increased photosynthetic step energy during the first two hours may consist of only white LEDs simulating morning hours, the next five hours may consist of only 50% white LEDs and 50% 660 nm red LEDs simulating noon and afternoon hours and the remaining hours may consist of 80% 660 nm red and 20% 720 nm red LEDs simulating sunset hours.

Figure 22:
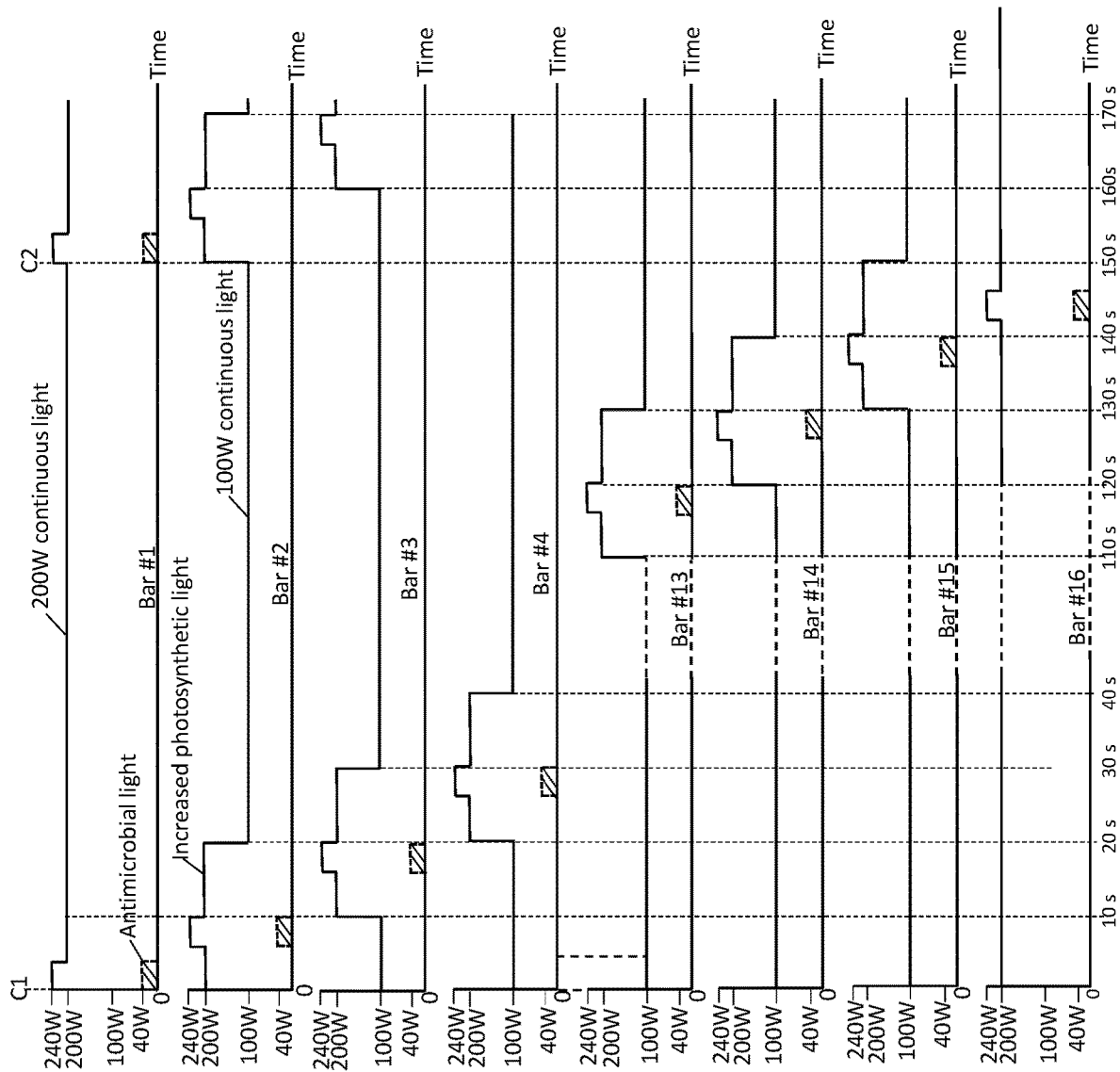

FIG. 22 illustrates a growing program for a flowering phase plant where increased step energy in an interior bar overlaps the increased step energy in the next interior bar. Because of light superimposition, light intensity will further increase during the overlap period. Increased lights that are generated by two light bars simultaneously will also add, that is, superimpose from various angles causing increased canopy penetration from sides. Wattage is shown on the left. C1 and C2 indicating Cycle 1 and Cycle 2, repeating cycles of wattage change across 16 Bars as in the example LED Array of FIG. 18, 1800. Bars #1-4 and #13-16 are shown for ease of example. Bars #5-12 would receive the same pattern of light in sequence. Sequences may repeat in ascending or descending order. Photosynthetic light wattage may be increased in steps to bars in sequence, additionally antimicrobial light may be provided in small pulses in each bar in sequence. As before short pulses of antimicrobial light may be 0.1 to 20 s and photosynthetic light may be pulsed and varied for as little as 1 s, or less, or up to 60 s, or more. Total power consumption for this lighting program of FIG. 22 would equal 1957 W, being 50% step 200 W and 50% 100 W, fixed 200×2, fixed 100×14 equal 195 0 W+17% of step at 40 W, microbial=1957 W.

Figure 23:
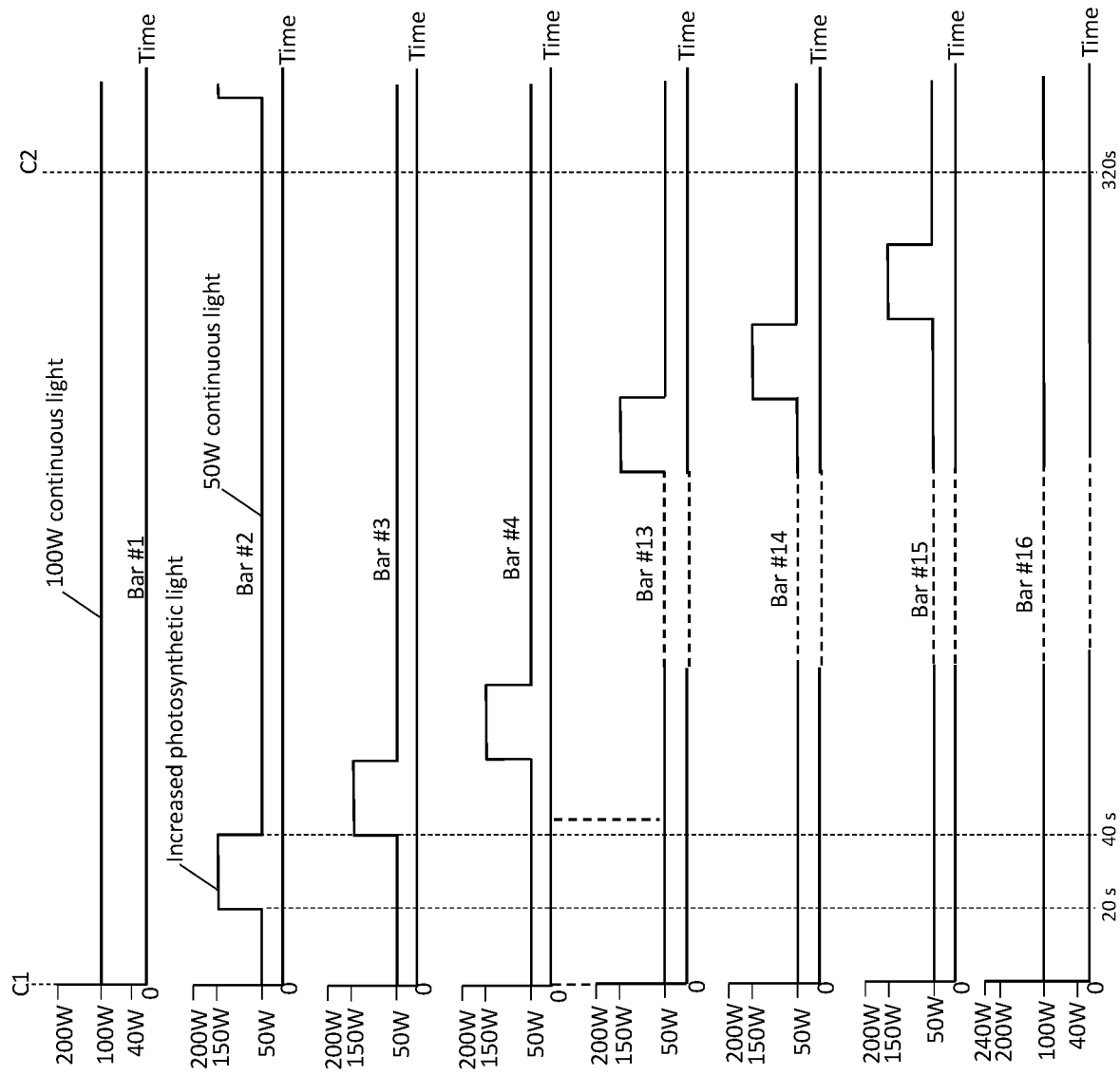

FIG. 23 illustrates how step increase light sweeping can be used to tackle grow operation during peak demand period or during air-conditioning malfunction or operation with emergency power generator. Utility company rate increases by many fold during peak demand period and without cooling temperature in the grow room will increase fast. By reducing energy consumption in the light bars by more than 60%, for example, energy cost and temperature can be kept low. Increased step light sweeping permits operation at 60% or even at less power because the increased step light sweeping from bar to bar will ensure above threshold photosynthetic activity. In FIG. 23, wattage is listed on left side, C1 and C2 indicate cycle number, repeating cycles of wattage change across 16 Bars as in the example LED array of FIG. 18, 1800. Bars #1-4 and #13-16 are shown for ease of example. Bars #5-12 would receive the same pattern of light in sequence. Total power consumption for this lighting program would equal 1000 W.

Figure 24:
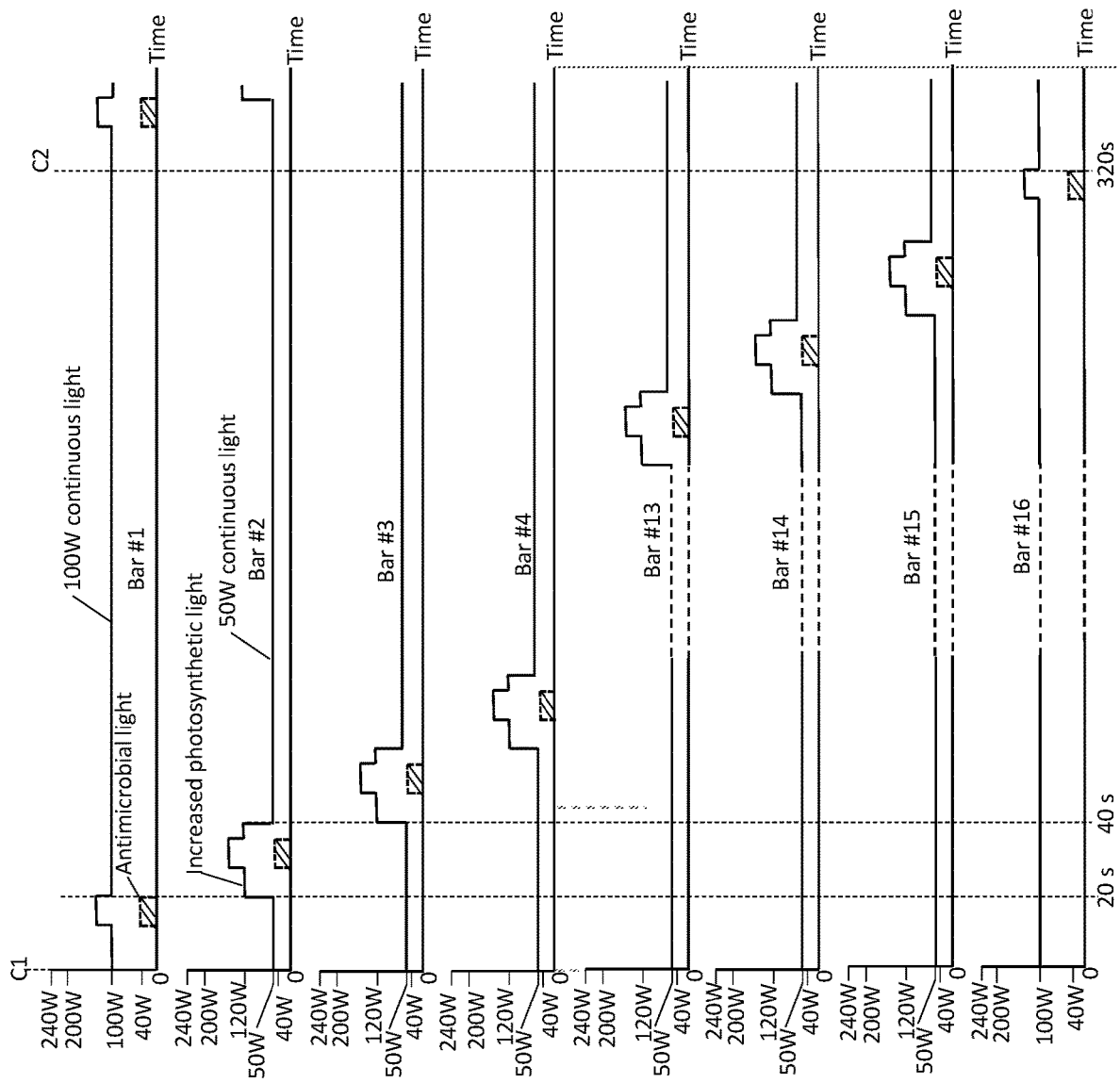

FIG. 24 illustrates an example of a growing program for a vegetative plant phase over time, with wattage listed on left side, C1 and C2 to indicated cycle number, repeating cycles of wattage change across 16 Bars as in the example LED Array of FIG. 18, 1800. Bars #1-4 and #13-16 are shown for ease of example. Bars #5-12 would receive the same pattern of light in sequence. As mentioned above vegetative plants are smaller and may have reduced light needs, therefore power can be saved by lowering wattage delivered to light bars. Total power consumption for this lighting program would equal 856 W.

It should be noted that even with increasing and decreasing wattage to bars and individual LED chips, light is always provided. No dark periods exist, power or wattage is decreased or increased, but (never stopped) whether 100 W or 10 W a minimum power exists in the light bars. This provides light uniformity while increasing sequentially either entire bar wattage or groups of LED chip wattage balances needs of growing plants with power consumption.

Lighting programs may be designed for vegetative and flowering phases of grow periods. It is a customized program and derived by a cultivator. This invention provides flexibilities and options to maximize harvest by saving energy. Therefore, depending on the cultivator, during a daily 12 hour flowering period, the lighting program could be three different types. For example, First lighting program for first 3 hours, second lighting program for next 7 hours and third lighting program for last 2 hours. First lighting program may consist periodic step energy increase that involves white light only to simulate morning hours. Second lighting program may consist periodic step energy increase that involves 660 nm red light only to simulate late morning to early afternoon hours and third lighting program may consist periodic step energy increase that involves 630 nm and 730 nm red lights to simulate late afternoon hours. Similarly, during vegetative phase the periodic light sweep may consist of 450 nm blue light.

The lighting program also provide options for selecting various periodic step energy increase sweep schemes. For example, two light bars at a time or sweeping step energy increase from left to right light bars then right to left light bars or left to middle bars then right to middle bars. The lighting program could be such that the periodic step energy increase would skip one or few light bars, for example, the middle light bar.

Figure 25:
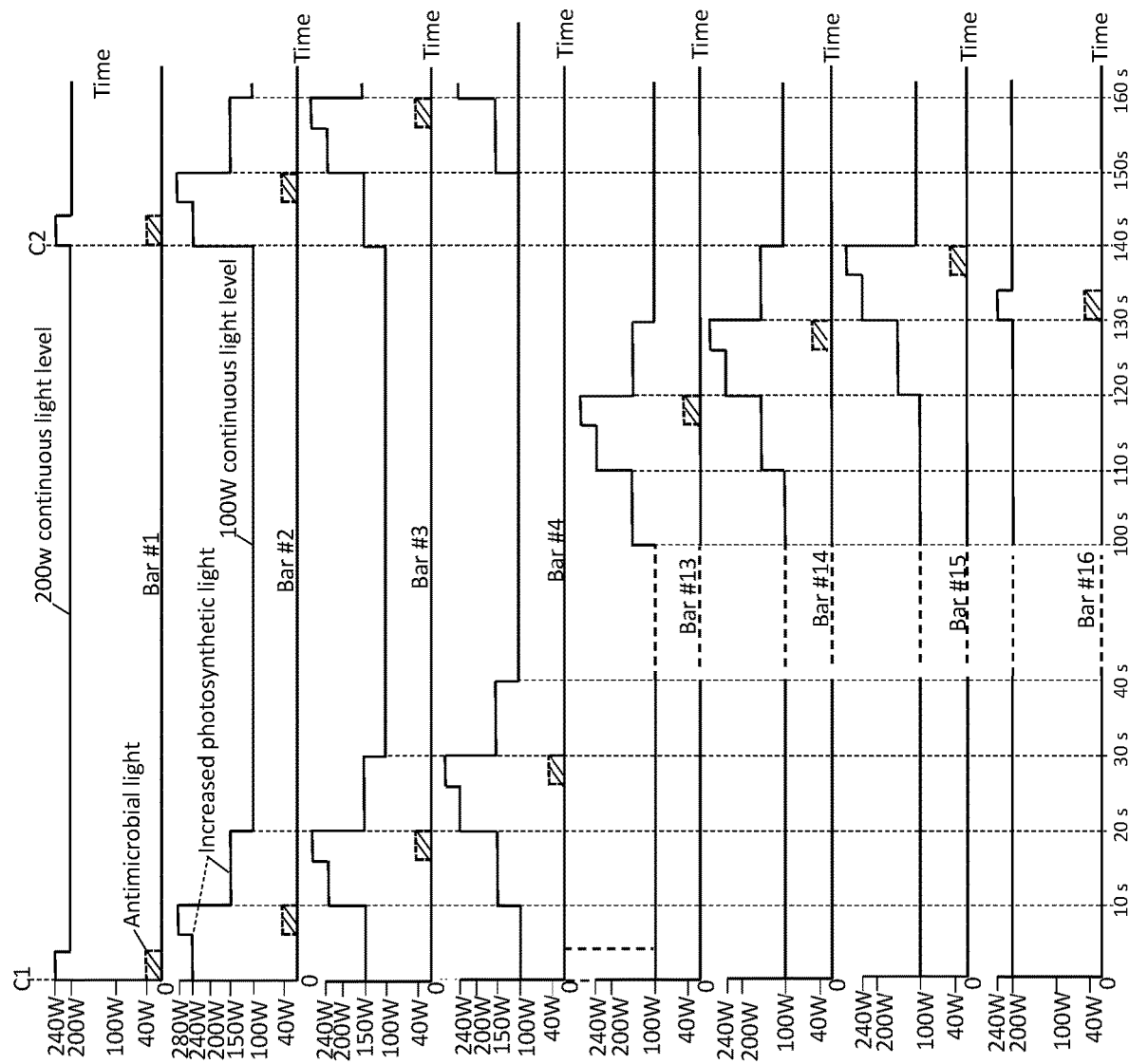

FIG. 25 illustrates another example flowering phase lighting program. The LED array contains sixteen light bars with 200 W continuous power provided to the first and last bars #1 and #16, and 100 W of continuous power provided to the interior bars #2-15. In this example three interior bars simultaneously receive increased photosynthetic light, center bar 200 W and the bar to its left and the bar to its right receive 50 W. The bars, in series, may be provided pulses of antimicrobial light via antimicrobial LED chips of selected wavelength as defined above for as little as 0.000005 seconds, or 0.00005 s, or 0.0005 s, or 0.005 s, or 0.05 s, or 0.5 s, or 1 s or longer. These pulses may comprise powering the antimicrobial LEDS with as little of 1 W, or 5 W, or 10 W, or 20 W, or 50 W, or more. In addition additional power may be fed to various interior bars with periodic increase or decrease. For instance, bar #2 may be powered at 240 W for 8 seconds, then 280 W for 2 s, then power could be decreased to 150 W for 10 s, then step down to 100 W. Following the first power step increase for Bar #2, Bar 3 # could be powered at 150 W for 10 s, 240 for 8 s, 280 W or 2 s, then 150 W for 10 s, then to 100 W. Following the first power step increase for Bar #3, Bar #4 could begin the program followed by Bar #3. You may want to repeat this cycle for each bar in sequence or a set of for instance two bars, or three bars, or more. The cycle may repeat in ascending or descending order. In this program, the photosynthetic energy equaled 1800 W with 233 W average increased photosynthetic energy. Antimicrobial energy of 50 W for 5 seconds each bar provides 20 W average antimicrobial energy for total power consumption of 2053 W.

Figure 26:
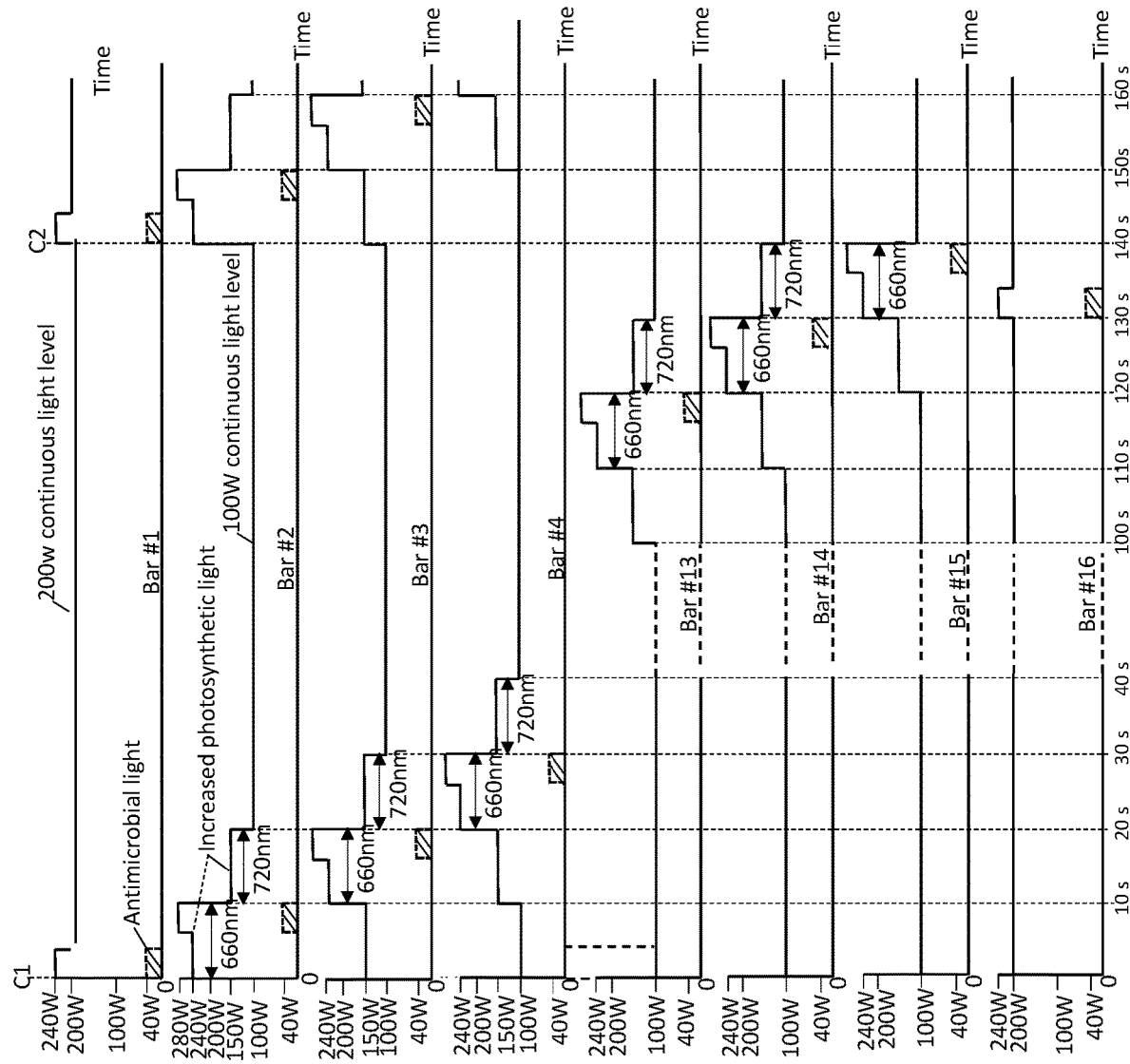

FIG. 26. is a variation of the growing program of FIG. 21 wherein in FIG. 26 increased photosynthetic energy consists of mixing 140 W 660 nm red LEDs with 50 W 720 nm red LEDs for 50% of the time to create the Emerson enhancement effect for further increase in amount of photosynthesis. In this arrangement a set of at least two or three interior light bars could cycle through the same program, or a set of sequential bars could operate simultaneously, or a set of three bars could have a center bar with 140 W and the other two bars given 50 W. Because light is additive, superimposing light, especially at angles would help light penetrate the plant canopy, therefore giving the whole plant better light delivery.

Figure 27:
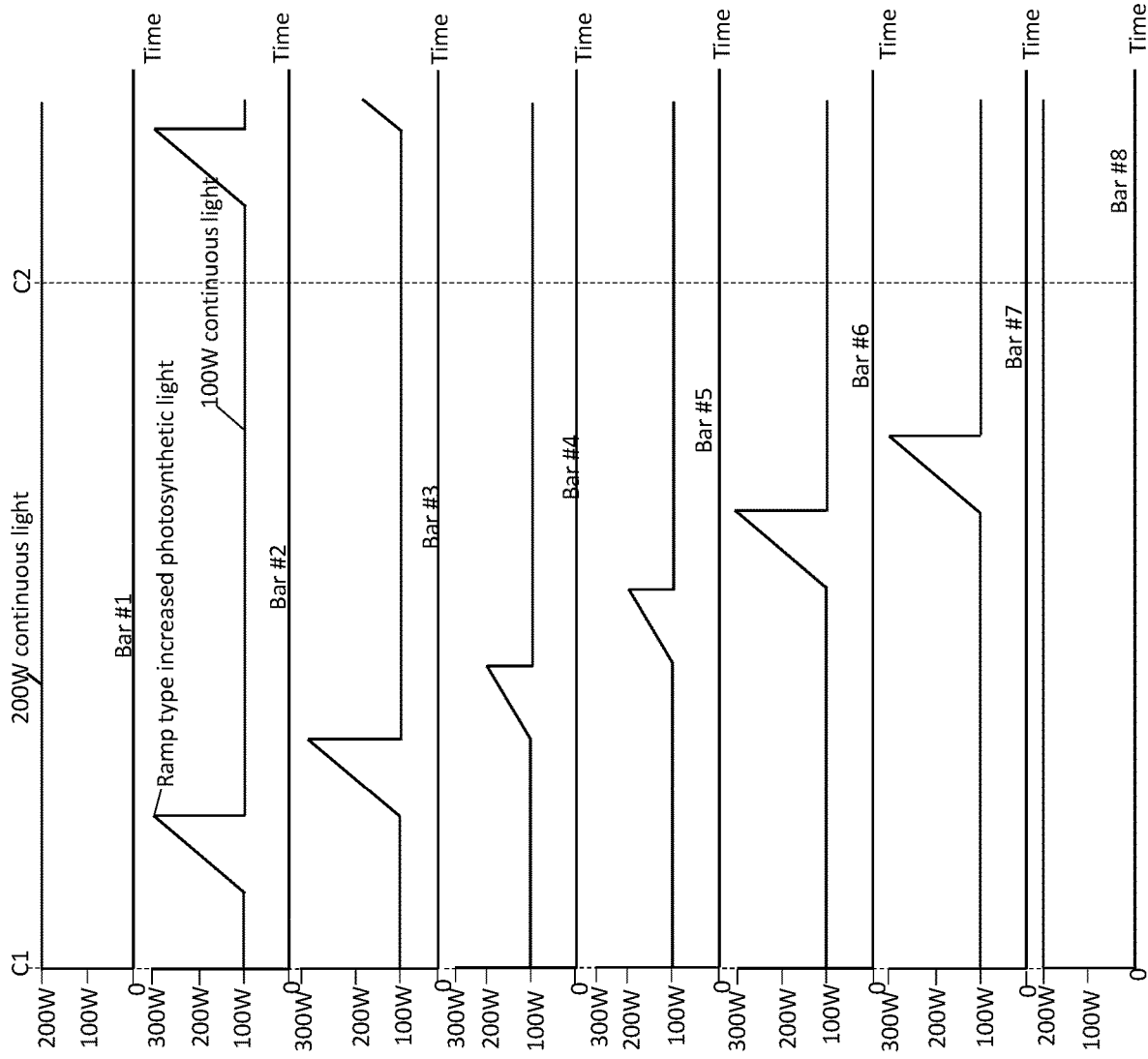

In the prior examples and figures we have described stepped increases of power in the lighting program for example increasing or decreasing with a jump in power of 5 W or 10 W or more as shown in the prior examples. Power increases, for either photosynthetic LED chips or antimicrobial LED chips, and/or decreases may also be continuous in that power may be increased in one light bar over a give period to time and in turn the power in the next light bar will be increased gradually to a certain power level over a given period of time. A lighting program indicating this type of gradual and continuous power increase in the photosynthetic LED chips within light bars in a cyclical manner is illustrated in FIG. 27. In FIG. 27 the lighting program is such that light bars #1 and #8 are provided a continuous stream of 200 W power, while light bars #2-7 start with an initial feed of 100 W. In sequence beginning with light bar #2 power is increased for a given amount of time for examples over at least 1 s, or at least 5 s, or at least 10 s, or at least 20 s, or at least 30 s, or at least 60 s or more to 300 W, as shown in Bars #2 and #3, or 200 W, as shown for bars #4 and #5. Like FIG. 19, the total energy consumption for a lighting program shown in FIG. 27 is approximately 1083 W. Power may be increased a small amount from the initial feed, for examples at least 5 W, or 10 W, or 20 W, or 50 W, or larger amounts such as 75 W, 100 W, or 200 W, or more depending on plant type and needs. An example In this way the wattage graph takes on a triangular pattern of increase and decrease in temperature. As it is shown in this example, once the power reaches a certain point it is brought back down to the initial feed of power nearly instantaneously, but this decrease may also happen over time for example over 1 s, or 2 s, or 5 s, or 10 s, or 20 s, or 30 s, or more. Antimicrobial LEDs may be powered for shorter duration in lower amounts of power increases over the array.

Figure 28:
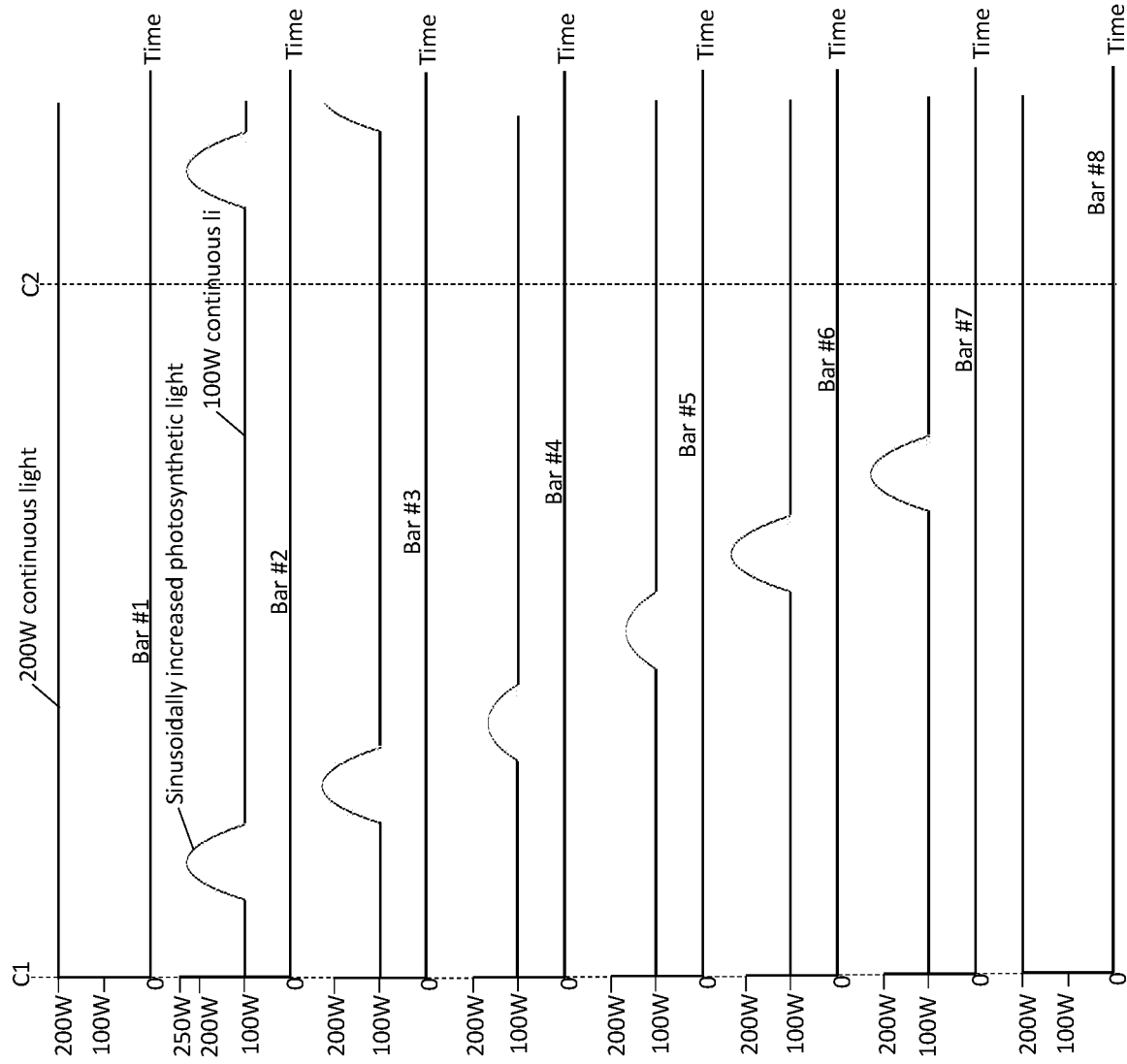

FIG. 28 illustrates a lighting program wherein the photosynthetic LEDs are powered with a power program taking on a sinusoidal profile of power increases and decreases in the light bars. FIG. 28 shows a sinusoidal type increased energy. In this case, bar #2, Bar #3, Bar #6, and Bar #7 has 100 W initial energy feed with approximately 141 W peak energy feed. Bar #4 and Bar #5 has 50 W initial energy feed with 65 W peak energy feed. As with FIGS. 19 and 27, the total energy consumption is approximately 1083 W. These sinusoidal shaped energy feeds may occur over at least 2 s, or at least 3 s, or at least 4 s, or at least 5 s, or 10 s, or at least 30 s or more. Energy feed may be increased for photosynthetic LEDs at least 5 W, or 10 W, or 50 W, or 100 W, or 150 W, or 200 W, or 300 W, or more. As explained in FIG. 27 description energy feed to antimicrobial LEDs may take on a similar pattern to that shown in FIG. 28 but time and energy amounts may be decreased to reduce harm to plants and workers.

Although the present invention has been described with reference to the disclosed embodiments and examples, numerous modifications and variations can be made and still the result will come within the scope of the invention. No limitation with respect to the specific embodiments disclosed herein is intended or should be inferred. Each apparatus and apparatus embodiment described herein has numerous equivalents.

PUBLICATIONS CITED

1. Yonglan Tian et al., "Effects of periodic photoinhibitory light exposure on physiology and productivity of Arabidopsis plants grown under low light", Journal of Experimental Botany, 2017 Jul. 10; 68(15): 4249-4262.
2. Akvil'e Viršil, et al., "The Comparison of Constant and Dynamic Red and Blue Light Irradiation Effects on Red and Green Leaf Lettuce", Published: 17 Nov. 2020, Agronomy, EISSN 2073-4395, Published by MDP.
3. Jonathan Gillespie et al., "Efficacy of pulsed 405-nm Light-Emitting Diodes for Antimicrobial Photodynamic Inactivation: Effects of intensity, Frequency, and Duty Cycle" Photomedicine and Laser Surgery, Volume 35, Number 3, 2017.
4. M. Kanechi et al., "Effects of pulsed lighting based light-emitting diodes on the growth and photosynthesis of lettuce leaves", International Society for Horticultural Science, ISHS Acta Horticulture 1134: VIII International Symposium on Light in Horticulture.
5. Michio Kanechi, "Growth and Photosynthesis under Pulsed Lighting", Sep. 19, 2018, DOI: 10.5772/intechopen.75519.
6. Michelle Maclean et al., "A New Proof of Concept in Bacterial Reduction: Antimicrobial Action of Violet-Blue Light (405 nm) in Ex Vivo Stored Plasma", Hindawi Publishing Corporation, Journal of Blood Transfusion, Volume 2016, Article ID 2920514.
7. Chukuka S Enwemeka, "Antimicrobial Blue Light: An Emerging Alternative to Antibiotics", Photomedicine and Laser Surgery, October 2013.
8. Jeff Gavin, "Sanitizing Light: LEDs Becoming a Disinfectant Technology", Electrical Contractor, Published on May 15, 2019.
9. Valeria Angarano et al., "Visible Light as an Antimicrobial Strategy for Inactivation of *Pseudomonas fluorescens* and *Staphylococcus epidermidis* Biofilms", Antimicrob Resist Infect Control 8, 14 (2019).
10. Jeswal, Punam, "Mechanisms of Photosynthesis" Plant Physiology, B.Sc (Hons.) Part III.
11. Lysenko et al. "Far-Red Spectrum of Second Emerson Effect: A Study Using Dual-Wavelength Pulse Amplitude Modulation Fluorometry" American Journal of Biochemistry and Biotechnology, Nov. 19, 2014

What is claimed is:

1. A LED grow light array for increasing plant canopy light penetration without increasing energy consumption, providing antimicrobial light to eliminate microorganism on plant, providing pulsing canopy penetrating and microbial light without a dark period, the LED grow light array comprising:
   a) a LED grow light array, the array comprising at least four light bars, wherein the light bars comprise discrete photosynthetic LED chips of different types based on the wavelength of light they emit, the light they emit being either blue, red, or white light, or a combination thereof, wherein blue light wavelength ranges from 405 nm to 450 nm, red light wavelength ranges from 600 nm to 720 nm, and white light is a combination of wavelengths that ranges from 400 nm to 700 nm, each type of photosynthetic LED chip forming a set of chips;
   b) wherein the bars are spaced evenly over a given plant growing area;
   c) wherein the light bars further comprise discrete antimicrobial LED chips of different types based on the wavelength of light they emit, the light being light with antimicrobial properties between the wavelengths of 100 nm and 405 nm, each type forming a set of chips;
   d) wherein each light bar comprises a circuit board to mount said discrete photosynthetic and antimicrobial LED chips thereon;
   e) at least one LED driver to provide power to the LED chips;
   f) at least one microprocessor to control the at least one LED driver; and
   g) a lighting program sent to the microprocessor designed to control the at least four light bars and the sets of photosynthetic and antimicrobial LED chips individually.

2. The LED grow light array of claim 1, wherein at least one set of the photosynthetic LED chips are powered throughout the lighting program with at least 1 W.

3. The LED grow light array of claim 2, wherein the antimicrobial LED chips are not powered unless specified by the lighting program.

4. A LED grow light array for increasing plant canopy light penetration without increasing energy consumption, providing antimicrobial light to eliminate microorganism on plant, providing pulsing canopy penetrating and microbial light without a dark period, the LED grow light array comprising:
   a) a LED grow light array, the array comprising at least four light bars, wherein the light bars comprise discrete photosynthetic LED chips of different types based on the wavelength of light they emit, the light they emit being either blue, red, or white light, or a combination thereof, wherein blue light wavelength ranges from 405 nm to 450 nm, red light wavelength ranges from 600 nm to 720 nm, and white light is a combination of wavelengths that ranges from 400 nm to 700 nm, each type of photosynthetic LED chip forming a set of chips;
   b) wherein the bars are spaced evenly over a given plant growing area;
   c) wherein the light bars further comprise discrete antimicrobial LED chips of different types based on the wavelength of light they emit, the light being light with antimicrobial properties between the wavelengths of 100 nm and 405 nm, each type forming a set of chips;

d) wherein each light bar comprises a circuit board to mount said discrete photosynthetic and antimicrobial LED chips thereon;
e) at least one LED driver to provide power to the LED chips;
f) at least one microprocessor to control the at least one LED driver; and
g) a lighting program sent to the microprocessor designed to control the at least four light bars and the sets of photosynthetic and antimicrobial LED chips individually;
h) wherein at least one set of the photosynthetic LED chips are powered throughout the lighting program with at least 1 W;
i) wherein the antimicrobial LED chips are not powered unless specified by the lighting program; and
j) wherein the lighting program designates different amounts of energy to be provided to the outer and inner light bars of the array.

5. The LED grow light array of claim 4, wherein the lighting program designates that the outer light bars receive more continuous power than the inner light bars.

6. The LED grow light array of claim 4, wherein the lighting program designates that the light bars, in sequential order, receive increased amounts of power for a given amount of time.

7. The LED grow light array of claim 6, wherein the lighting program repeats the sequential order of designating increase amounts of power for a given amount of time.

8. The LED grow light array of claim 6, wherein the lighting program repeats, in reverse order, the sequential order of designating increase amounts of power for a given amount of time.

9. The LED grow light array of claim 6 wherein the given amount of time is at least 0.05 seconds.

10. The LED lighting array of claim 4, wherein the lighting program designates that the light bars receive at least two pulses of additional power in a row beginning with the first light bar and moving to the next light bar sequentially, the pulses being at least 0.05 seconds each.

11. The LED grow light array of claim 4, wherein the lighting program designates that the light bars receive at least three pulses of additional power in a row beginning with the first light bar and moving to the next light bar sequentially, the pulses being at least 0.05 seconds each.

12. The LED grow light array of claim 4, wherein the lighting program designates that the light bars receive at least four pulses of additional power in a row beginning with the first light bar and moving to the next light bar sequentially, the pulses being at least 0.05 seconds each.

13. The LED grow light array of claim 4, wherein the lighting program designates an initial power feed to all the light bars and therein after designates increased power to each light bar in sequential order for a given period of time.

14. The LED grow light array of claim 4, wherein the lighting program designates an initial power feed to all the light bars and therein after designates increased power to the interior light bars in sequential order for a given period of time.

15. The LED grow light array of claim 14 wherein the lighting program designates a higher initial power feed to the outside light bars than the inside light bars.

16. The LED grow light array of claim 4, wherein the lighting program designates a higher power feed for the set of photosynthetic LED chips emitting 660 nm for a given period of time in each bar sequentially.

17. The LED grow light array of claim 16, wherein the given period of time is at least 0.05 seconds.

18. The LED grow light array of claim 4, wherein the lighting program designates a higher power feed for the set of photosynthetic LED chips emitting 450 nm for a given period of time in each bar sequentially.

19. The LED grow light array of claim 18, wherein the given period of time is at least 0.05 seconds.

20. The LED grow light array of claim 4, wherein the lighting program designates a higher power feed for the set of photosynthetic LED chips emitting 730 nm for a given period of time in each bar sequentially.

21. The LED grow light array of claim 20, wherein the given period of time is at least 0.05 seconds.

22. The LED grow light array of claim 4, wherein the lighting program designates a higher power feed for the set of antimicrobial LED chips emitting 385 nm for a given period of time in each bar sequentially.

23. The LED grow light array of claim 22, wherein the given period of time is at least 0.000005 seconds.

24. The LED grow light array of claim 4, wherein the lighting program designates that at least some photosynthetic LED chips are powered and at least one set of antimicrobial LED chips are powered on for each light bar sequentially with at least 1 W for at least 0.000005 seconds.

25. The LED grow light array of claim 1 further comprising wireless communication means for the microprocessor.

26. The LED grow light array of claim 1, wherein the lighting program sets an initial level of light for each light bar and the photosynthetic LED sets thereon, and wherein thereafter increases and decreases in power to light bars are continuous to reach a designated power amount over a designated amount of time.

27. The LED grow light array of claim 4, wherein the lighting program designates an initial power amount for the photosynthetic LED chips in all light bars for a $1^{st}$ set time period, thereafter power to the photosynthetic LED chips in at least one light bar is increased to a level 2 power amount for a $2^{nd}$ set time period, thereafter power to the photosynthetic LED chips in the at least one light bar is increased to a level 3 power amount for a $3^{rd}$ set time period, and thereafter the power to the photosynthetic LED chips in the at least one light bar is reset to the initial power amount.

28. The LED grow light array of claim 27, wherein a pulse of power is sent to at least some of the antimicrobial LED chips in each light bar in sequence for a time period of at least 0.000005 s.

29. The LED grow light array of claim 27, wherein after the power to the photosynthetic LEDs in the at least one light bar is increased to the level 2 power for the $2^{nd}$ set time period, power to the photosynthetic LEDs of a next light bar in the sequence is increased to the level 2 power for the $2^{nd}$ set time period, and thereafter power to the photosynthetic LED chips in the next light bar is increased to the level 3 power amount for the $3^{rd}$ set time period, and thereafter the power to the photosynthetic LED chips in the next light bar is reset to the initial power amount.

30. A method for lighting a grow area, the method comprising the steps of:
a) providing a LED grow light array, the array comprising at least four light bars spaced evenly over the grow area, wherein the light bars comprise discrete photosynthetic LED chips of different types based on the wavelength of light they emit, the light they emit being either blue, red, or white light, or a combination thereof, wherein blue light wavelength ranges from 405 nm to 450 nm, red light wavelength ranges from 600 nm to 720 nm, and white light is a combination of wavelengths that ranges from 400 nm to 700 nm, each type of photosynthetic LED chip forming a set of chips;

b) providing on the light bars discrete antimicrobial LED chips of different types based on the wavelength of light they emit, the light being light with antimicrobial properties between the wavelengths of 100 nm and 405 nm, each type forming a set of chips, wherein the antimicrobial LED chips are not powered unless specified by the program;

c) providing a driver to power the light bars and discrete sets of LED chips;

d) providing a microprocessor to control the driver, the microprocessor capable of receiving a lighting program which designates how the driver is controlled; and e) providing a lighting program designed to control the at least four light bars and the sets of photosynthetic and antimicrobial LED chips individually.

31. The method of claim 30 further comprising providing the lighting program to the microprocessor via wireless means.

\* \* \* \* \*